US010973670B2

(12) United States Patent
Wu et al.

(10) Patent No.: US 10,973,670 B2
(45) Date of Patent: Apr. 13, 2021

(54) ADJUSTABLE BRACE

(71) Applicant: INDUSTRIAL TECHNOLOGY RESEARCH INSTITUTE, Hsinchu (TW)

(72) Inventors: Tzong-Ming Wu, Taipei (TW); Ji-Bin Horng, Tainan (TW); Sung-Ho Liu, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 242 days.

(21) Appl. No.: 16/229,845

(22) Filed: Dec. 21, 2018

(65) Prior Publication Data

US 2019/0374364 A1 Dec. 12, 2019

Related U.S. Application Data

(60) Provisional application No. 62/682,491, filed on Jun. 8, 2018.

(30) Foreign Application Priority Data

Dec. 19, 2018 (TW) .................................. 107145879

(51) Int. Cl.
*A61F 5/00* (2006.01)
*A61F 5/01* (2006.01)
(Continued)

(52) U.S. Cl.
CPC ...... *A61F 5/0123* (2013.01); *A63B 21/00181* (2013.01); *A63B 21/4011* (2015.10);
(Continued)

(58) Field of Classification Search
CPC .. A61F 5/00; A61F 5/01; A61F 5/0123; A61F 2005/0125; A61F 2005/0137;
(Continued)

(56) References Cited

U.S. PATENT DOCUMENTS 4,699,129 A * 10/1987 Aaserude et al. .... A61F 5/0123
602/16
5,395,304 A * 3/1995 Tarr et al. ............. A61F 5/0125
602/26

(Continued)

FOREIGN PATENT DOCUMENTS

| CN | 104822346 B | 5/2018 |
|---|---|---|
| TW | M458211 U | 8/2013 |
| TW | I522093 B | 2/2016 |

OTHER PUBLICATIONS

Electromyographic and biomechanic analysis of anterior cruciate ligament deficiency and functional knee bracing, Dan K. Ramsey et al., Clinical Biomechanics, 2003, p. 28-34.

(Continued)

*Primary Examiner* — Alireza Nia
*Assistant Examiner* — Michael Milo
(74) *Attorney, Agent, or Firm* — Locke Lord LLP; Tim Tingkang Xia, Esq.

(57) ABSTRACT

The disclosed embodiments provide an adjustable brace including a first wearable part, a second wearable part, an angle adjustment mechanism and a resistance mechanism. The first wearable part and the second wearable part are pivotably connected to each other via the angle adjustment mechanism and the resistance mechanism.

14 Claims, 15 Drawing Sheets

(51) Int. Cl.
*A63B 21/00* (2006.01)
*B25J 9/00* (2006.01)

(52) U.S. Cl.
CPC .. *A63B 21/4025* (2015.10); *A61F 2005/0155* (2013.01); *A61F 2005/0167* (2013.01); *A63B 2220/24* (2013.01); *B25J 9/0006* (2013.01)

(58) Field of Classification Search
CPC ...... A61F 2005/0141; A61F 2005/0148; A61F 2005/0176; A61F 2005/0132; A61F 2005/0134; A61F 2005/0155; A61F 2005/0167; A63B 21/4011; A63B 21/4025; A63B 21/00181; A63B 2220/24; B25J 9/0006
USPC .................... 601/5; 602/16, 26; 16/239, 260
See application file for complete search history.

(56) References Cited

U.S. PATENT DOCUMENTS

| | | | | |
|---|---|---|---|---|
| 5,788,618 A | * | 8/1998 | Joutras | A63C 10/145 482/114 |
| 5,899,869 A | * | 5/1999 | Barrack | A61F 5/0125 602/16 |
| 5,921,946 A | * | 7/1999 | Tillinghast et al. | A61F 5/0123 602/16 |
| 5,954,621 A | * | 9/1999 | Joutras et al. | A63B 21/4025 482/114 |
| 6,517,504 B1 | * | 2/2003 | Postelmans | A61F 5/0123 602/26 |
| 7,156,818 B2 | * | 1/2007 | Salmon et al. | A61F 5/0125 602/5 |
| 7,963,933 B2 | | 6/2011 | Nace | |
| 8,425,439 B1 | * | 4/2013 | McKeon et al. | A61F 5/0125 602/16 |
| 8,753,301 B2 | * | 6/2014 | Tran | A61F 5/0102 602/16 |
| 8,915,873 B2 | | 12/2014 | Kim et al. | |
| 9,132,026 B2 | | 9/2015 | Bledsoe et al. | |
| 9,220,622 B2 | | 12/2015 | Ingimundarson et al. | |
| 9,265,647 B2 | | 2/2016 | Desousa | |
| 9,610,188 B2 | | 4/2017 | Walsh et al. | |
| 9,615,955 B2 | | 4/2017 | Bledsoe | |
| 9,682,005 B2 | | 6/2017 | Herr et al. | |
| 2011/0009786 A1 | * | 1/2011 | Chan | A61F 5/0125 602/16 |
| 2015/0150705 A1 | * | 6/2015 | Capra et al. | A61F 5/0123 602/6 |
| 2016/0120267 A1 | * | 5/2016 | Burns et al. | A43C 11/165 24/68 C |
| 2017/0312153 A1 | | 11/2017 | Paul et al. | |
| 2017/0367852 A1 | | 12/2017 | Kazerooni et al. | |

OTHER PUBLICATIONS

Functional bracing of ACL injuries: current state and future directions, Sean D. Smith et al., Knee Surg Sports Traumatol Arthrosc, 2014.
Functional Knee Brace Altered Predicted Knee Muscle and Joint Forces in People with ACL Reconstruction During Walking, Paul Devita et al., J. of Applied Biomechanics, 2001, p. 297-311.
Taiwan Patent Office, "Office Action", dated Aug. 13, 2019, Taiwan.

* cited by examiner

ADJUSTABLE BRACE

CROSS-REFERENCE TO RELATED APPLICATIONS

This non-provisional application claims priority under 35 U.S.C. § 119(a) on provisional patent application No. U.S. 62/682,491 filed in U.S.A. on Jun. 8, 2018, and on patent application No(s) 107145879 filed in Taiwan R. O. C. on Dec. 19, 2018, the entire contents of which are hereby incorporated by reference.

TECHNICAL FIELD

The present disclosure relates to an adjustable brace, more particularly to an adjustable brace having an angle adjustment mechanism and a resistance mechanism.

BACKGROUND

The rehabilitation is an important phase after an anterior cruciate ligament reconstruction. And the motion of the knee joint should be restricted during the early phase of rehabilitation. A knee brace is a common practice for enhancing knee stability after rupture of the anterior cruciate ligament or reconstruction for restricting the movable range of the knee as well as in knee unloading. However, as the progression along the rehabilitation continuum and phases, appropriate exercises will help to strengthen the muscles around the knee and help the patients to regain full range of motion. A brace having an adjustable range of rotation and resistance will be very helpful in the rehabilitation exercise programs.

Therefore, muscle strength training is required to avoid muscle atrophy during the knee joint or other joint rehabilitations, especially for those who had been through the anterior cruciate ligament reconstruction. However, there is yet no knee or another joint brace is capable of training muscle strength.

SUMMARY

Accordingly, the present disclosure provides an adjustable brace not only has an angle adjustment mechanism but also has a resistance mechanism.

According to one aspect of the present disclosure, an adjustable brace including a first wearable part, a second wearable part, an angle adjustment mechanism and a resistance mechanism. The first wearable part and the second wearable part are pivotably connected to each other via the angle adjustment mechanism and the resistance mechanism.

According to the adjustable brace discussed above, the adjustable brace has the angle adjustment mechanism for adjusting the pivotable range of the first wearable part and the second wearable part relative to each other and the resistance mechanism for increasing resistance to the pivotal movement of the first wearable part and the second wearable part. Therefore, the adjustable brace can not only restrict the movable range motion of the knee joint which has been undergone the anterior cruciate ligament reconstruction but also can provide resistance to the motion of the joint to properly train the muscle around the joint, thereby improving the effect of the rehabilitation.

BRIEF DESCRIPTION OF THE DRAWINGS

The present disclosure will become better understood from the detailed description given hereinbelow and the accompanying drawings which are given by way of illustration only and thus are not intending to limit the present disclosure and wherein.

DETAILED DESCRIPTION

Figure 1A:
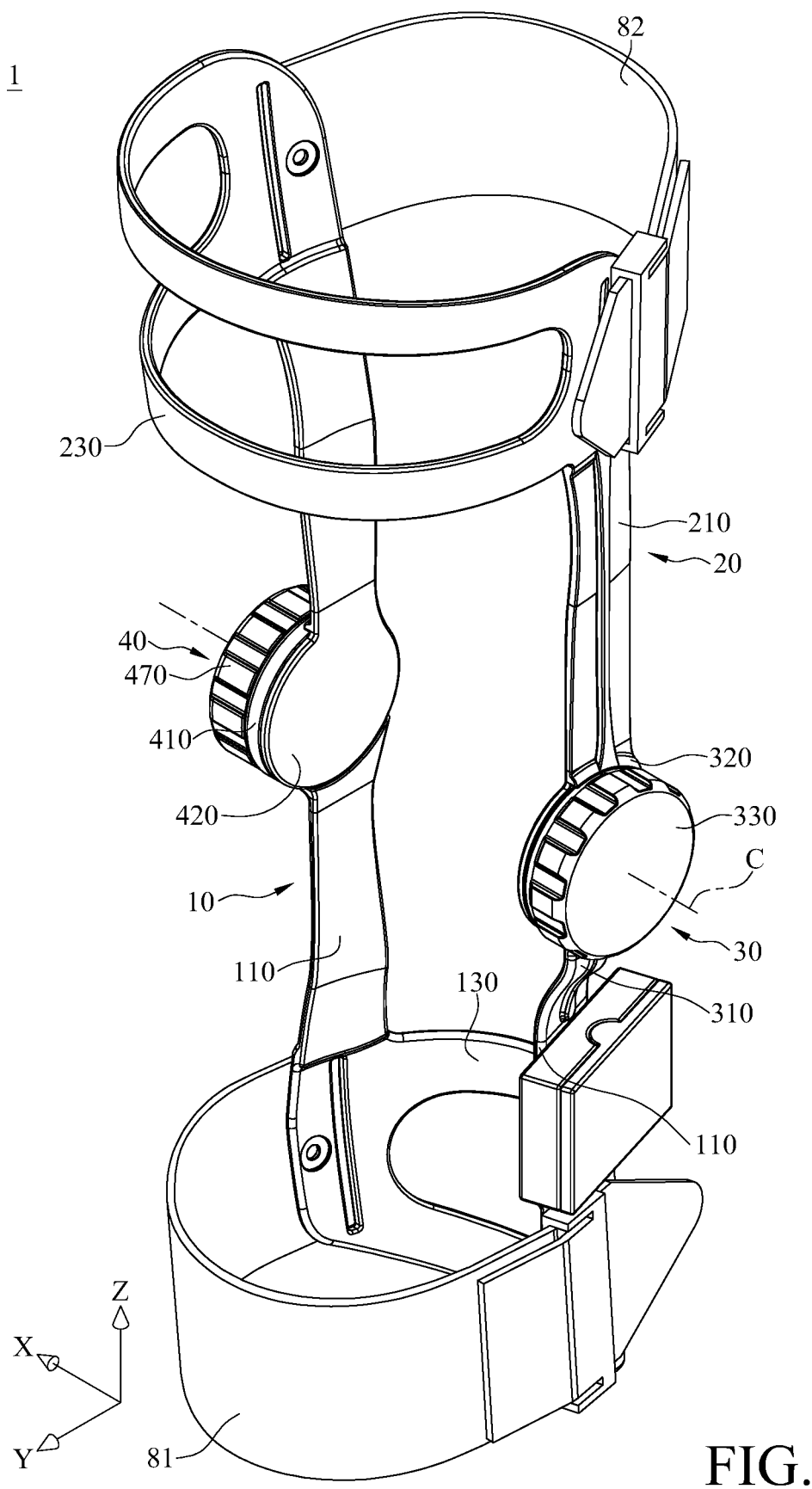
FIG. 1A to 1B are perspective views of an adjustable brace according to one embodiment of the present disclosure taken at different perspectives.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In addition, the terms used in the present disclosure, such as technical and scientific terms, have its own meanings and can be comprehended by those skilled in the art, unless the terms are additionally defined in the present disclosure. That is, the terms used in the following paragraphs should be read on the meaning commonly used in the related fields and will not be overly explained unless the terms have a specific meaning in the present disclosure. Furthermore, in order to simplify the drawings, some conventional structures and components are drawn in a simplified manner to keep the drawings clean.

Further, the following embodiments are disclosed by the figures, and some practical details are described in the following paragraphs, but the present disclosure is not limited thereto. Furthermore, for the purpose of illustration, some of the structures and components in the figures are simplified, and wires, lines or buses are omitted in some of the figures. And the size, ratio, and angle of the components in the drawings of the present disclosure may be exaggerated for illustrative purposes, but the present disclosure is not limited thereto, and various modifications are allowed and can be made according to the following disclosure as long as it does not depart from the spirit of the present disclosure. Note that the actual size and designs of the product manufactured based on the present disclosure may also be modified according to any actual requirements.

Further, the terms, such as "end", "portion", "part", "area" and the like may be used in the following to describe specific components and structures or specific features thereon or therebetween, but are not intended to limit these components and structures. In the following, it may use terms, such as "substantially", "approximately" or "about"; when these terms are used in combination with size, concentration, temperature or other physical or chemical properties or characteristics, they are used to express that, the deviation existing in the upper and/or lower limits of the range of these properties or characteristics or the acceptable tolerances caused by the manufacturing tolerances or analysis process, would still able to achieve the desired effect.

Furthermore, unless otherwise defined, all the terms used in the disclosure, including technical and scientific terms, have their ordinary meanings that can be understood by those skilled in the art. Moreover, the definitions of the above terms are to be interpreted as being consistent with the technical fields related to the disclosure. Unless specifically defined, these terms are not to be construed as too idealistic or formal meanings. The terms of the components in the disclosure are sometimes referred to in a more concise manner, depending on the requirements of the description, and should be understood by the reader.

Figure 1B:
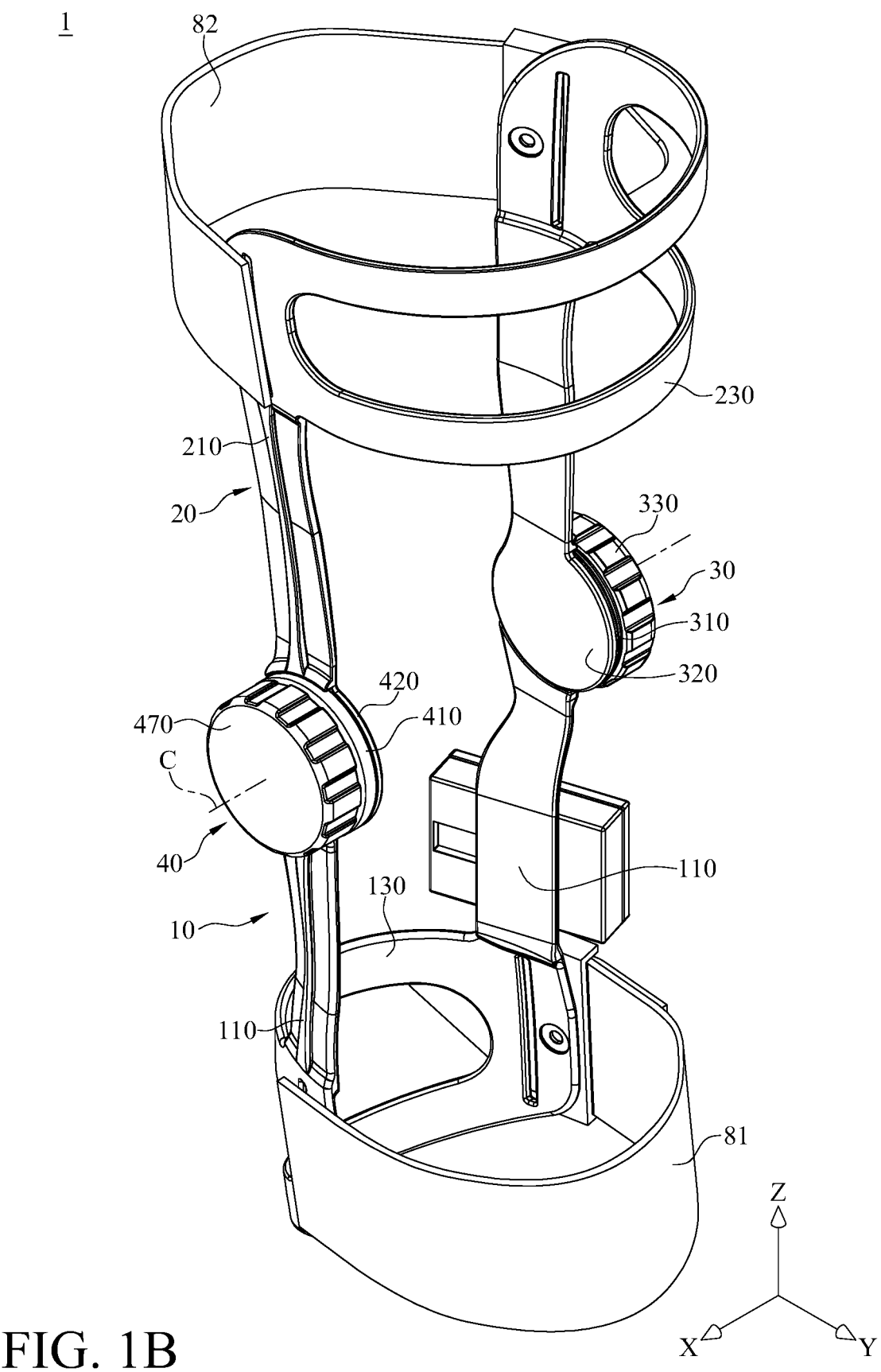

Please refer to FIG. 1A to 1B, which are perspective views of an adjustable brace according to one embodiment of the present disclosure taken at different perspectives.

This embodiment provides an adjustable brace 1. The adjustable brace 1 is suitable for, for example, knee joint, but the present disclosure is not limited thereto. A person skilled in the art can obtain suggestions and be able to manufacture an adjustable brace suitable for elbow joint based on the descriptions and teachings of the adjustable brace described below.

In addition, in this and some embodiments, the adjustable brace can be made by the cooperation of the 3D (three-dimensional) scanning technology and 3D printing technology. In detail, the 3D scanner can scan and obtain the physical appearance information of limbs, and then an adjustable brace exclusively for the wearer will be created by the orthotic specialists based on the above physical appearance information and then printed with a 3D printer. Therefore, the adjustable brace will perfectly fit the injured part of the wearer. In addition, a further adjustment requested by the patient with respect to the physical appearance information is available added before being printed by the 3D printer. Further, the materials of the adjustable brace include, for example but not limited to, polymer such as nylon that can be repeatedly deformed and has the ability to return from deformation. The above personalized processes make the adjustable brace perfect-fitting, such that the adjustable brace is not only cost-effective and high flexible but also helps considerably improve the rehabilitation, specifically for young-aged patient who are still in growing-up stage and need to keep buying new and bigger adjustable brace as they grow up and for those who had suffered from stroke and need to buy different adjustable brace with respect to different phases of rehabilitation.

In addition, since the 3D printing can build a complex geometries such as lattice or honeycomb structure, the adjustable brace of this and some embodiments may be lightweight and strong in structural strength, thereby reducing the weight while wearing. And the adjustable brace may be made from a composite material so that a single component of the adjustable brace may have hard and soft portions at the same time. For example, one of the components of the adjustable brace may have a soft inner layer and a hard outer layer or a specific distribution of hard and soft portions that matches the injured joint so as to improve the practicality, comfort, and durability. Moreover, with the help of the 3D printing technology, the adjustable brace may have porous structures or hollow features so as to make the adjustable brace more lightweight and breathable.

Furthermore, since the adjustable brace of this and some embodiments can be fabricated by the abovementioned personalized processes, it can be understood that the following contents such as the relationship between the adjustable brace and the injured joint is only used for illustrating one of the suggestions for making the adjustable brace depending on the wearer's injured joint, but the disclosure is not limited by the condition of the wearer's injured joint or the size shown in the drawings.

As shown in the figure, in this embodiment, the adjustable brace 1 includes a first wearable part 10, a second wearable part 20, an angle adjustment mechanism 30, a resistance mechanism 40, a first strap 81 and a second strap 82. It is noted that the abovementioned components or mechanisms are exemplary of the present disclosure, and the present disclosure is not limited thereto.

The first wearable part 10 and the second wearable part 20 are pivotably connected to each other via the angle adjustment mechanism 30 and the resistance mechanism 40, such that the first wearable part 10 and the second wearable part 20 can be pivoted to each other about a pivot axis C, thereby allowing the knee to bend and straighten.

Further, the first wearable part 10 includes two first side parts 110 and a first curved part 130. The first side parts 110 and the first curved part 130 are suitably in contact with the limbs around the injured joint. As the manufacture process discussed above, it can be understood that the first side parts 110 and the first curved part 130 may be perfect-fitting with respect to the wearer's limbs so as to improve the wearing comfort.

The two opposite ends of the first strap 81 are detachably assembled to the two opposite ends of the first curved part 130. Specifically, one end of the first strap 81 is detachably fixed to one end of the first curved part 130, and the other end of the first strap 81 is adjustably engaged with a buckle structure (not numbered) on the other end of the first curved part 130. Accordingly, the first strap 81 is detachable with respect to the first wearable part 10, such that the size of the space between the first strap 81 and the first curved part 130 can be adjusted so as to modify the tightness of the first strap 81 on the limb. In addition, the first strap 81 may have an array of recesses (not shown) to make it easier to be bent or deformed.

However, the first strap 81 and the quantity thereof are not restricted and can be modified according to the actual requirements. For example, in another embodiment, the adjustable brace may include two first straps 81. Alternatively, in some other embodiments, there may be no first strap on the adjustable brace; in this case, the shape of the first wearable part may be altered so that the side parts are able to be directly attached and fixed onto the wearer's limb, but the present disclosure is not limited thereto.

The angle adjustment mechanism 30 and the resistance mechanism 40 are located on, for example, sides of the wearer's injured joint (e.g., knee joint). The angle adjustment mechanism 30 includes a first angle-adjustment-mechanism connecting part 310 and a second angle-adjustment-mechanism connecting part 320. The first angle-adjustment-mechanism connecting part 310 and the second angle-adjustment-mechanism connecting part 320 are pivotably connected to each other. The resistance mechanism 40 includes a first resistance-mechanism connecting part 410 and a second resistance-mechanism connecting part 420. The first resistance-mechanism connecting part 410 and the second resistance-mechanism connecting part 420 are pivotably connected to each other. In addition, in this embodiment, the angle adjustment mechanism 30 may further include an angle adjustment knob 330 configured to adjust the pivotable range of the first angle-adjustment-mechanism connecting part 310 and the second angle-adjustment-mechanism connecting part 320 relative to each other. The resistance mechanism 40 may further include a resistance adjustment knob 470 configured to adjust the friction between the first resistance-mechanism connecting part 410 and the second resistance-mechanism connecting part 420. The details of the angle adjustment mechanism 30 and the resistance mechanism 40 will be described later.

As shown in the figures, the first angle-adjustment-mechanism connecting part 310 of the angle adjustment mechanism 30 and the first resistance-mechanism connecting part 410 of the resistance mechanism 40 are respectively connected to the first side parts 110 of the first wearable part 10. In this and some embodiments, the first angle-adjustment-mechanism connecting part 310 of the angle adjustment mechanism 30, the first resistance-mechanism connecting part 410 of the resistance mechanism 40, the first side parts 110 and the first curved part 130 may be, but not limited, made of a single piece. That is, the first angle-adjustment-mechanism connecting part 310 of the angle adjustment mechanism 30, the first resistance-mechanism connecting part 410 of the resistance mechanism 40 and the first wearable part 10 may be, but not limited, made of a single piece.

The second angle-adjustment-mechanism connecting part 320 of the angle adjustment mechanism 30 is pivotably disposed on the inner side of the first angle-adjustment-mechanism connecting part 310 of the angle adjustment mechanism 30. The second resistance-mechanism connecting part 420 of the resistance mechanism 40 is pivotably disposed on the inner side of the first resistance-mechanism connecting part 410 of the resistance mechanism 40. And the inner sides of the second angle-adjustment-mechanism connecting part 320 of the angle adjustment mechanism 30 and the second resistance-mechanism connecting part 420 of the resistance mechanism 40 may be additionally provided with soft pads (not shown) in order to improve the wearing comfort.

The second wearable part 20 includes two second side parts 210 and a second curved part 230. The second side parts 210 are respectively connected to the second angle-adjustment-mechanism connecting part 320 of the angle adjustment mechanism 30 and the second resistance-mechanism connecting part 420 of the resistance mechanism 40. The second curved part 230 is connected to the second side parts 210, and the second curved part 230 and the second side parts 210 may be, but not limited, made of a single piece. In this and some embodiments, the second angle-adjustment-mechanism connecting part 320 of the angle adjustment mechanism 30, the second resistance-mechanism connecting part 420 of the resistance mechanism 40, and the second side parts 210 and the second curved part 230 of the second wearable part 20 may be, but not limited, made of a single piece. That is, the second angle-adjustment-mechanism connecting part 320 of the angle adjustment mechanism 30, the second resistance-mechanism connecting part 420 of the resistance mechanism 40, and the second wearable part 20 may be, but not limited, made of a single piece. Similarly, as the manufacture process discussed above, the second side parts 210 and the second curved part 230 of the second wearable part 20 may be perfect-fitting with respect to another limb so as to improve the wearing comfort.

The two opposite ends of the second strap 82 are detachably assembled to the two opposite ends of the second curved part 230. Specifically, one end of the second strap 82 is detachably fixed to one end of the second curved part 230, and the other end of the second strap 82 is adjustably engaged with a buckle structure (not numbered) on the other end of the second curved part 230. Accordingly, the second strap 82 is detachable with respect to the second wearable part 20, such that the size of the space between the second strap 82 and the second curved part 230 can be adjusted so as to modify the tightness of the second strap 82 on limb. Similarly, the second strap 82 may have an array of recesses (not shown) to make it easier to be bent or deformed.

Similarly, the second strap 82 and the quantity thereof are not restricted and can be modified according to the actual requirements. For example, in another embodiment, the adjustable brace may include two second straps 82. Alternatively, in some other embodiments, there may be no second strap 82 on the adjustable brace; in this case, the shape of the second wearable part may be altered so that the side parts are able to be directly attached and fixed onto the wearer's limb, but the present disclosure is not limited thereto.

Figure 2A:
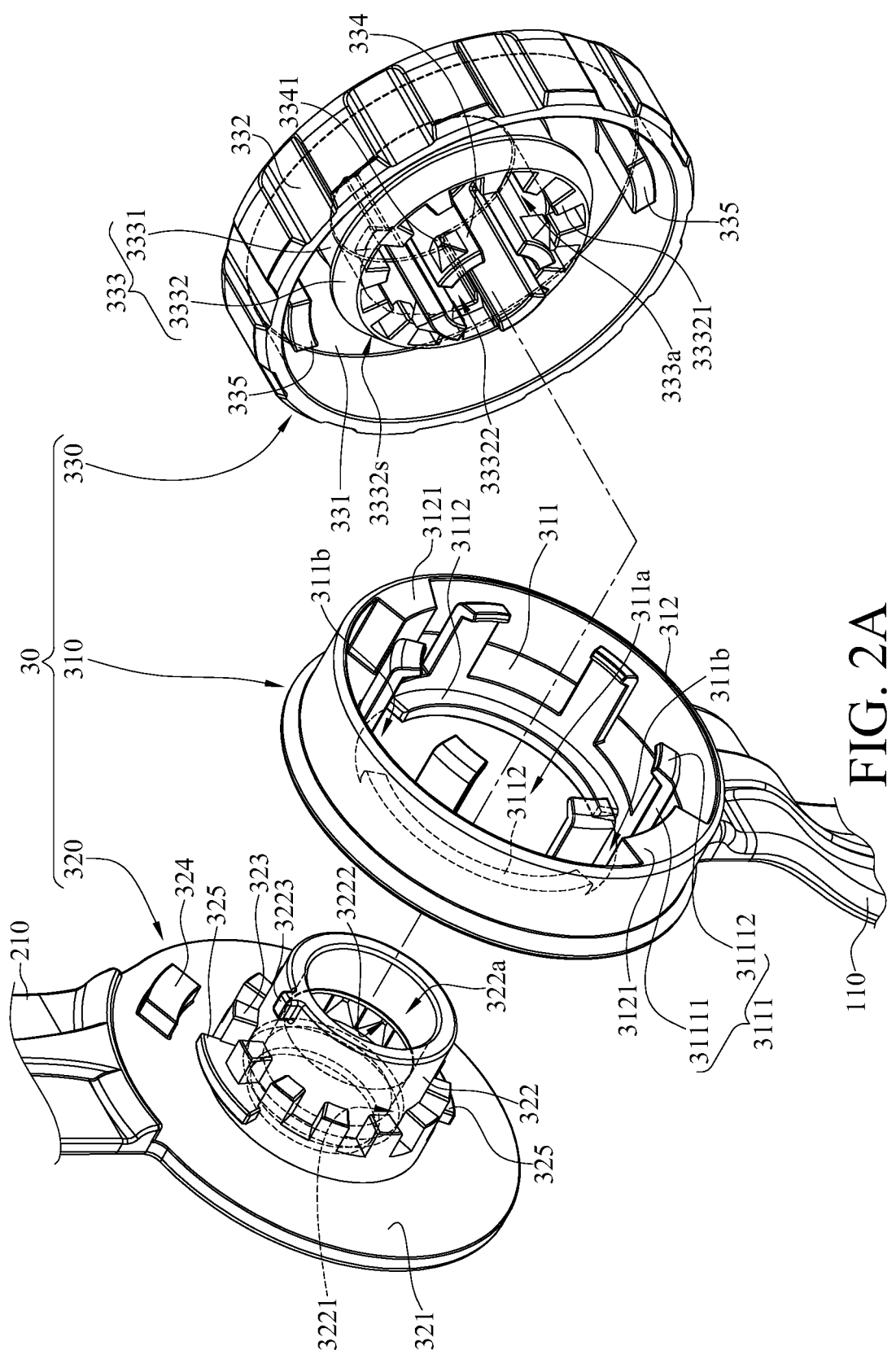
FIG. 2A to 2B are exploded views of an angle adjustment mechanism in FIG. 1 taken at different perspectives.
Figure 2B:
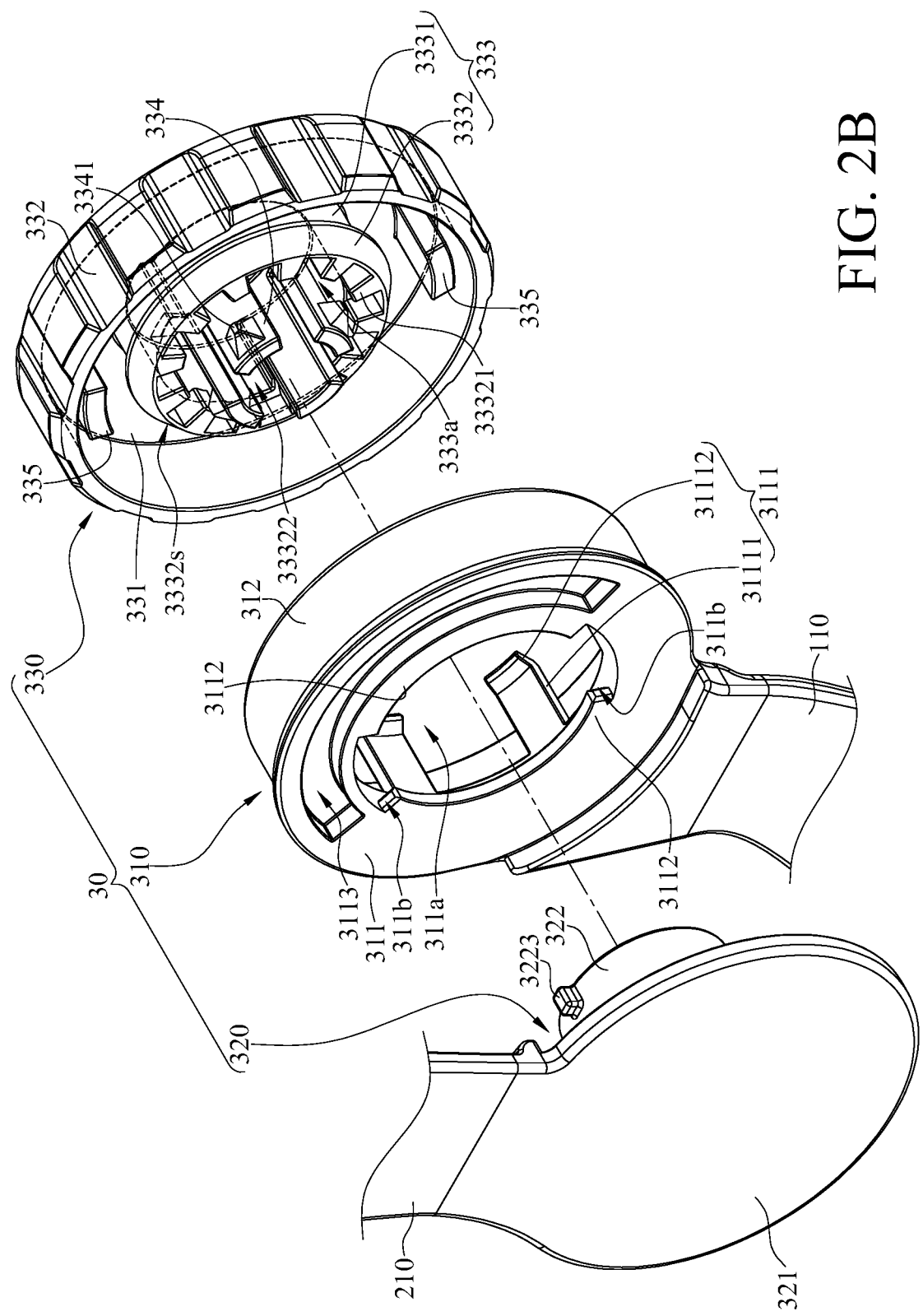
Figure 3:
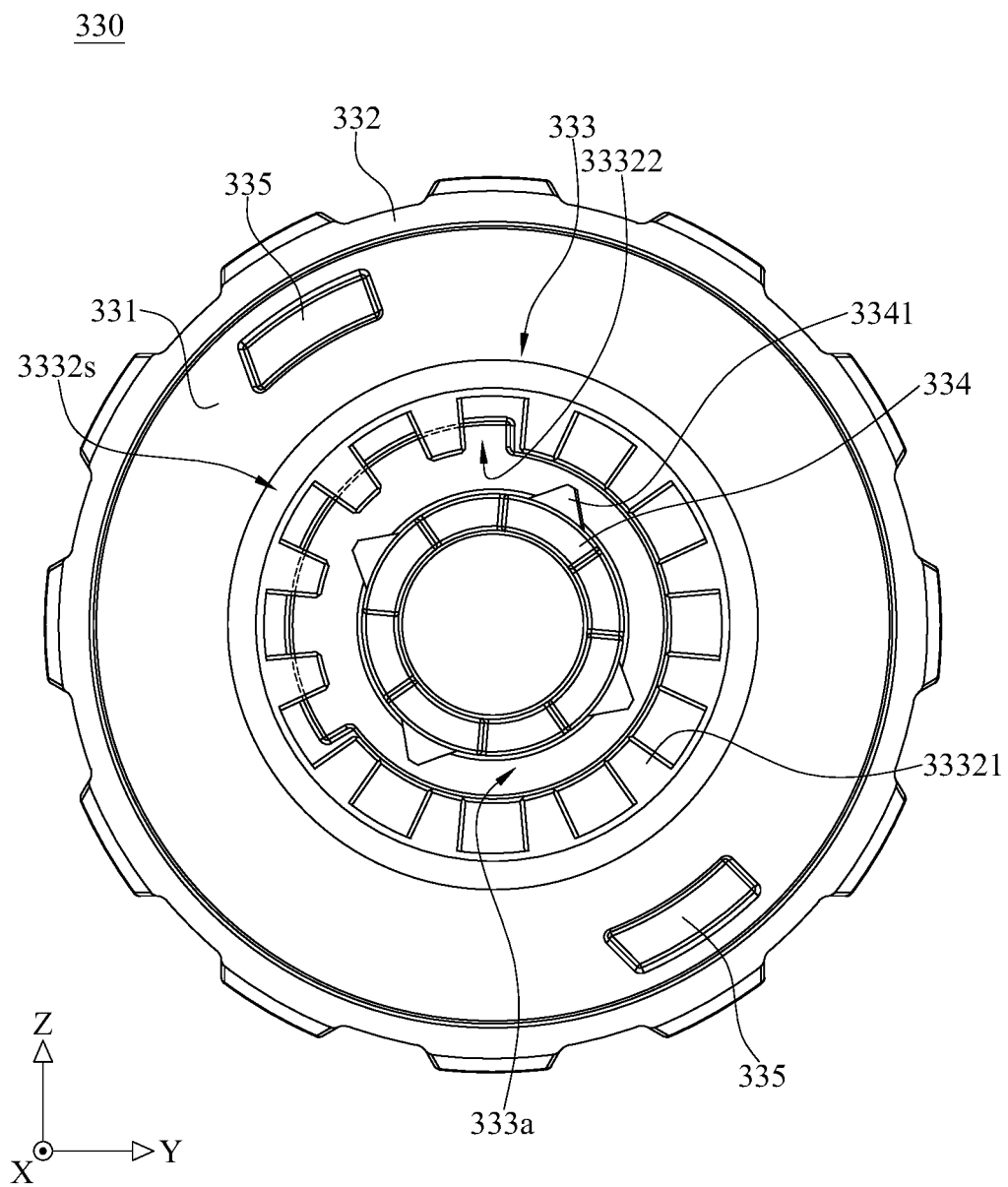
FIG. 3 is a front view of an angle adjustment knob of the angle adjustment mechanism in FIG. 1.

The angle adjustment mechanism 30 and the resistance mechanism 40 are described in more detail below. Please refer to FIG. 2A to 2B and FIG. 3, FIG. 2A to 2B are exploded views of the angle adjustment mechanism 30 taken at different perspectives, and FIG. 3 is a front view of the angle adjustment knob 330.

As described above, in this embodiment, the angle adjustment mechanism 30 includes the first angle-adjustment-mechanism connecting part 310, the second angle-adjustment-mechanism connecting part 320 and the angle adjustment knob 330.

The first angle-adjustment-mechanism connecting part 310 includes a base 311 and a sidewall part 312. The base 311 is ring-shaped like plate and has a through hole 311a, a plurality of retaining parts 3111, a plurality of engagement parts 3112 and a first groove 3113. The through hole 311a is located at the center of the base 311. The engagement parts 3112 are located at two sides of the through hole 311a and are separated from each other, such that notches 311b are formed therebetween and connected to the through hole 311a. In this embodiment, the quantity of the engagement parts 3112 is two, and the quantity of the notches 311b is two, but the present disclosure is not limited thereto.

The retaining parts 3111 are spaced apart from one another, and they surround the through hole 311a and extend toward the angle adjustment knob 330 from the second angle-adjustment-mechanism connecting part 320 of the base 311. Further, the retaining parts 3111 each include an arm portion 31111 and a hook portion 31112. The arm portions 31111 are substantially perpendicular to the base 311. The hook portions 31112 are located on a side of the arm portions 31111 away from the base 311 and extend inwards in radial directions. At least part of the through hole 311a along the edge of the through hole 311a is covered by the hook portions 31112 from the viewpoint along the pivot axis C. However, the present disclosure is not limited by the configuration and quantity of the retaining parts 3111.

The sidewall part 312 extends toward the angle adjustment knob 330 from the base 311 and surrounds the base 311. And there are two first movement limiting parts 3121 protrude inwards from different sides of the sidewall part 312, such that the first movement limiting parts 3121 are spaced apart from each other. It may also be considered that the first movement limiting parts 3121 protrude toward the angle adjustment knob 330 from the base 311. In this embodiment, the first movement limiting parts 3121 may be considered as the solid parts on opposite sides of two arc-shaped grooves (not numbered).

The first groove 3113 is located at a surface of the base 311 facing the second angle-adjustment-mechanism connecting part 320 and is substantially in an arc shape. Therefore, it is understood that the first groove 3113 faces away from the angle adjustment knob 330 and the aforementioned retaining parts 3111.

The second angle-adjustment-mechanism connecting part 320 of the angle adjustment mechanism 30 includes a base 321, an assembly cylinder 322, a plurality of first teeth 323, an assembly block 324, and two engagement parts 325. The assembly cylinder 322 is a hollow structure and extends toward the first angle-adjustment-mechanism connecting part 310 from the base 321. It may also be considered that the assembly cylinder 322 extends toward the angle adjustment knob 330 from the base 321. The outer diameter of the assembly cylinder 322 is smaller than the diameter of the through hole 311a of the aforementioned first angle-adjustment-mechanism connecting part 310. Further, the hollow assembly cylinder 322 has a bore 322a, and the hollow assembly 322 has a ring-shaped groove 3221 and a plurality of engagement recesses 3222 on an inner wall (not numbered) of the assembly cylinder 322 that forms the bore 322a. In more detail, the engagement recesses 3222 are located farther away from the base 321 than the ring-shaped groove 3221 and are consisted of a series of geometric recesses. In addition, the assembly cylinder 322 further has a protrusion 3223 protruding from the outer wall (not numbered) of the assembly cylinder 322 and locating at a side of the assembly cylinder 322 away from the base 321.

The first teeth 323 are disposed around the outer surface of the assembly cylinder 322. The assembly block 324 protrudes toward the first angle-adjustment-mechanism connecting part 310 from the base 321 and corresponds to the first groove 3113 of the first angle-adjustment-mechanism connecting part 310. The engagement parts 325 respectively protrude from two different sides of the assembly cylinder 322. The engagement parts 325 are located closer to the base 321 than the protrusion 3223 but are still spaced apart from the base 321. Further, the shapes of the engagement parts 325 substantially match the notches 311b of the aforementioned first angle-adjustment-mechanism connecting part 310.

The angle adjustment knob 330 is rotatably fixed to the assembly cylinder 322 of the second angle-adjustment-mechanism connecting part 320 and has at least two angle adjustment positions. Specifically, in this embodiment, the angle adjustment knob 330 includes a base 331, a sidewall part 332, a cylindrical part 333, a plurality of elastic arm parts 334 and two second movement limiting parts 335. The sidewall part 332 extends toward the first angle-adjustment-mechanism connecting part 310 from the base 331 and surrounds the base 331.

The cylindrical part 333 is a hollow structure and extends from the base 331 toward the first angle-adjustment-mechanism connecting part 310. It may also be considered that the cylindrical part 333 extends toward the second angle-adjustment-mechanism connecting part 320 from the base 331. The hollow cylindrical part 333 has a bore 333a. The diameter of the bore 333a is slightly larger than the outer diameter of the assembly cylinder 322 of the aforementioned second angle-adjustment-mechanism connecting part 320. Further, the cylindrical part 333 includes a neck portion 3331 and a head portion 3332 connected to each other. The neck portion 3331 is located between and connected to the base 331 and the head portion 3332. The outer diameter of the head portion 3332 is larger than the outer diameter of the neck portion 3331. The head portion 3332 has a guide slope 3332s at a side facing away from the base 331.

The cylindrical part 333 has a plurality of second teeth 33321 and a trench 33322. The second teeth 33321 protrude from an inner wall (not numbered) of the cylindrical part 333 and are located at a side of the head portion 3332 located away from the base 331. The trench 33322 is formed on the inner wall of the cylindrical part 333 and is located closer to the base 331 than the second teeth 33321. The trench 33322 is substantially in a U-shape and has two opposite openings (not numbered). One opening of the trench 33322 is located between two adjacent second teeth 33321 and exposed, and the other opening of the trench 33322 is located between another two adjacent second teeth 33321 and is also exposed.

The elastic arm parts 334 are disposed in the bore 333a of the cylindrical part 333 and extend toward the first angle-adjustment-mechanism connecting part 310 from the base 331. It may also be considered that the elastic arm parts 334 extend toward the second angle-adjustment-mechanism connecting part 320 from the base 331. The elastic arm parts 334 are spaced apart from one another and arranged in a circle. One end of the elastic arm part 334 facing away from the base 331 may be referred as a free end (not numbered). The elastic arm part 334 can be bent or deformed as a certain amount of force is applied on its free end. Further, the elastic arm parts 334 each have an engagement protrusion 3341 protruding from the outer surface (not numbered) of the free ends.

Further, the second movement limiting parts 335 are separated from each other, extend toward the first angle-adjustment-mechanism connecting part 310 from the base 331, and are located between the cylindrical part 333 and the sidewall part 332.

Figure 4A:
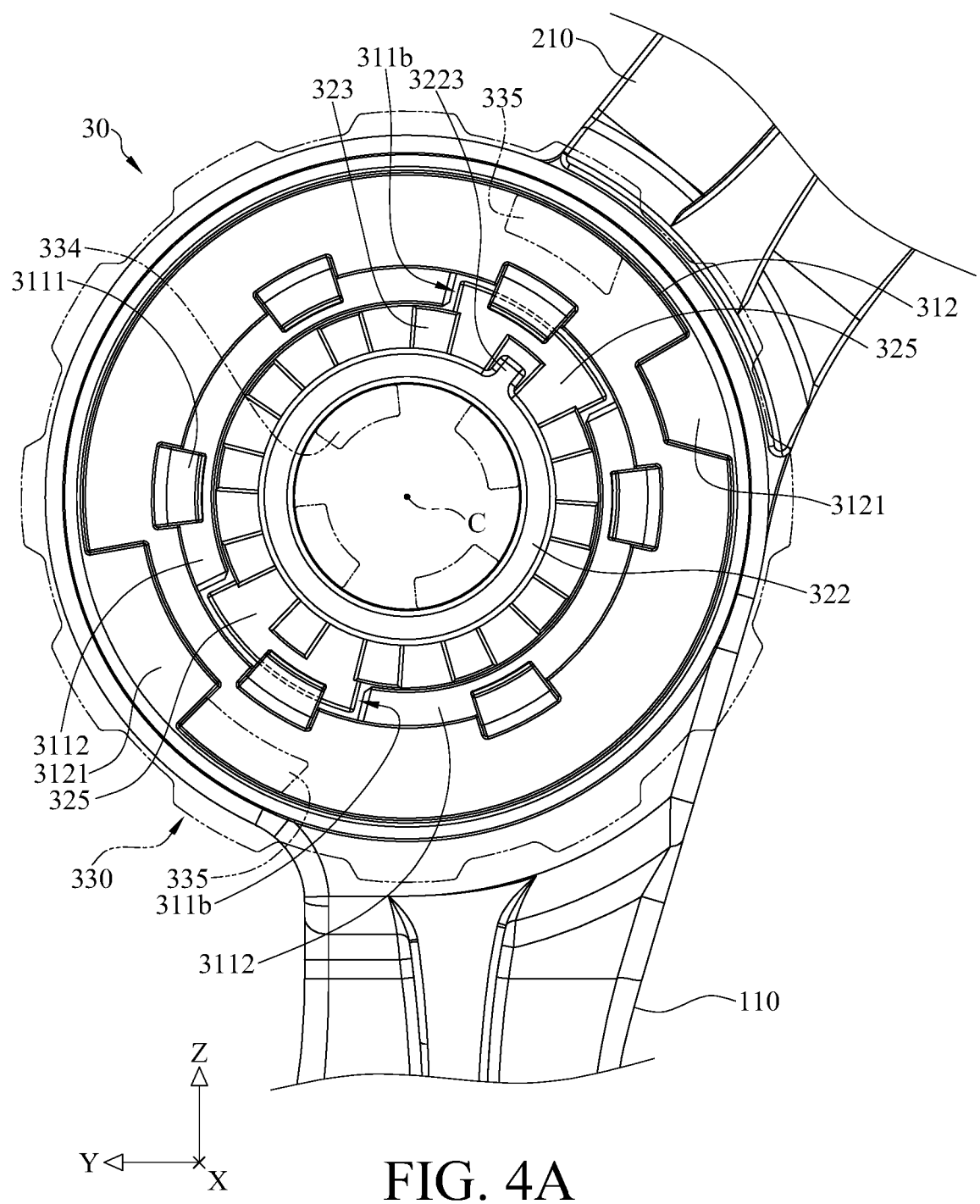
FIG. 4A is a partial side view of the angle adjustment mechanism in FIG. 1 as the angle adjustment mechanism is ready to be detached or assembled.
Figure 4B:
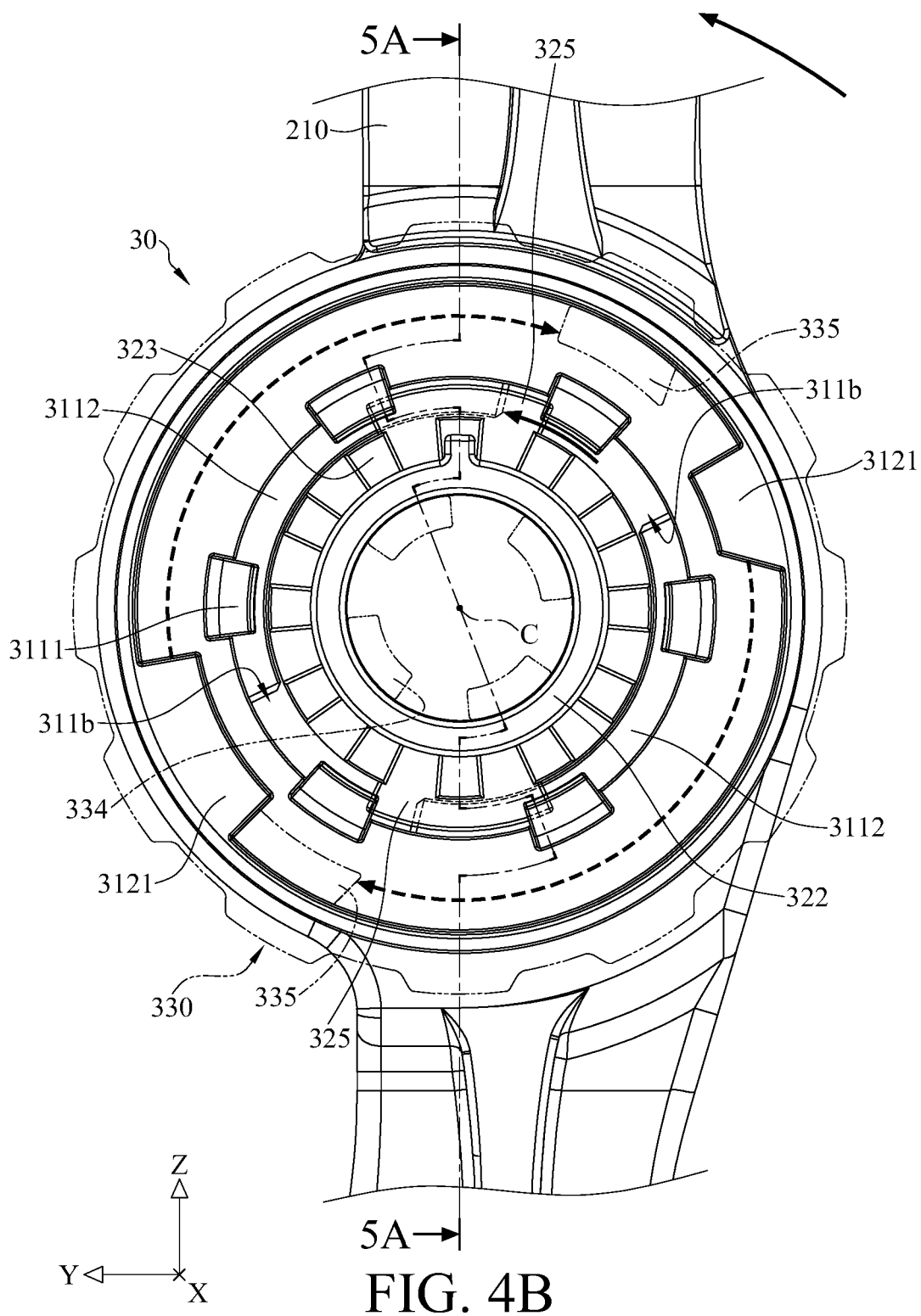
FIG. 4B is a partial side view of the angle adjustment mechanism in FIG. 1 after the angle adjustment mechanism has been assembled.

According to the auxiliary lines show in the figure, the first step to assemble the angle adjustment mechanism 30 may be to assemble the first angle-adjustment-mechanism connecting part 310 and the second angle-adjustment-mechanism connecting part 320. Please refer to FIG. 4A to 4B, FIG. 4A is a partial side view of the angle adjustment mechanism 30 as the angle adjustment mechanism 30 is ready to be detached or assembled, and FIG. 4B is a partial side view of the angle adjustment mechanism 30 after the angle adjustment mechanism 30 has been assembled.

Firstly, referring to FIG. 2A to 2B and FIG. 4, the engagement parts 325 of the second angle-adjustment-mechanism connecting part 320 can be placed into the notches 311b of the first angle-adjustment-mechanism connecting part 310, and the assembly block 324 of the second angle-adjustment-mechanism connecting part 320 can be placed into the first groove 3113 of the first angle-adjustment-mechanism connecting part 310. By doing so, the assembly cylinder 322 of the second angle-adjustment-mechanism connecting part 320 is allowed to be disposed into the through hole 311a of the base 311 of the first angle-adjustment-mechanism connecting part 310.

Then, referring to FIG. 2A to 2B and FIG. 4, the first angle-adjustment-mechanism connecting part 310 can be pivoted relatively to the second angle-adjustment-mechanism connecting part 320. During the pivotal movement, the engagement parts 3112 of the base 311 are clamped between the engagement parts 325 and the base 321 of the second angle-adjustment-mechanism connecting part 320. Accordingly, the first angle-adjustment-mechanism connecting part 310 will be fixed to the second angle-adjustment-mechanism connecting part 320, and the assembly block 324 of the second angle-adjustment-mechanism connecting part 320 is slidably located in the first groove 3113 of the first angle-adjustment-mechanism connecting part 310. Herein, it can be understood that the first groove 3113 restricts the movable range of the assembly block 324, namely restricts the pivotable range of the first angle-adjustment-mechanism connecting part 310 and second angle-adjustment-mechanism connecting part 320 relative to each other.

Then, referring to the auxiliary lines shown in FIG. 2A to 2B, the angle adjustment knob 330 can be assembled to the first angle-adjustment-mechanism connecting part 310 and the second angle-adjustment-mechanism connecting part 320. In detail, the sidewall part 332 of the angle adjustment knob 330 can be sleeved on the sidewall part 312 of the first angle-adjustment-mechanism connecting part 310. During this process, the head portion 3332 of the cylindrical part 333 of the angle adjustment knob 330 will contact the hook portions 31112 of the retaining parts 3111 of the first angle-adjustment-mechanism connecting part 310 with the guide slopes 3332s so as to force the arm portions 31111 to bend and push the hook portions 31112 outwards. As the angle adjustment knob 330 continuously moves toward the first angle-adjustment-mechanism connecting part 310, the hook portions 31112 will slide over the head portion 3332 and then engage with the neck portion 3331 of the cylindrical part 333. By doing so, the angle adjustment knob 330 can be fixed to the first angle-adjustment-mechanism connecting part 310 when the retaining parts 3111 hold the cylindrical part 333.

Additionally, as the guide slope 3332s of the head portion 3332 contacts the hook portions 31112, the protrusion 3223 on the assembly cylinder 322 of the second angle-adjustment-mechanism connecting part 320 can be aligned with one of the openings of the trench 33322 of the cylindrical part 333 of the angle adjustment knob 330 and thus allowing the cylindrical part 333 to be smoothly sleeved on the assembly cylinder 322, in other words, the assembly cylinder 322 will be able to be inserted into the bore 333a of the cylindrical part 333.

During the insertion of the assembly cylinder 322 of the second angle-adjustment-mechanism connecting part 320 into the bore 333a of the cylindrical part 333 of the angle adjustment knob 330, the elastic arm parts 334 of the angle adjustment knob 330 will also be inserted into the bore 322a of the assembly cylinder 322 so that the engagement protrusions 3341 of the elastic arm parts 334 can be selectively engaged with the engagement recesses 3222 of the assembly cylinder 322. Alternatively, the elastic arm parts 334 can be further inserted into the assembly cylinder 322 so that the engagement protrusions 3341 of the elastic arm parts 334 will be engaged with the ring-shaped groove 3221 of the assembly cylinder 322. As a result, the assembly of the angle adjustment mechanism 30 is completed.

Figure 5A:
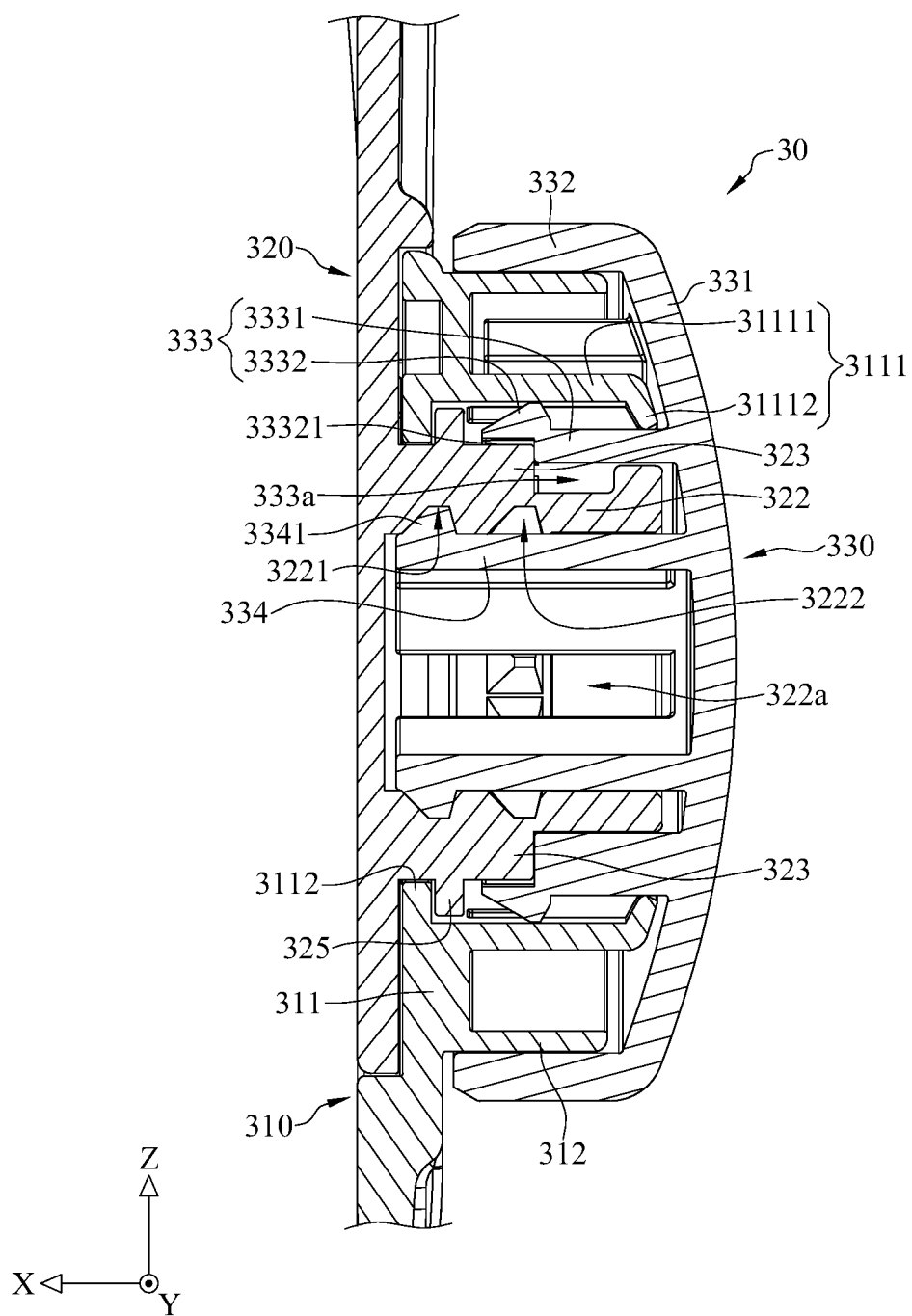
FIG. 5A is a cross-sectional view of the angle adjustment mechanism in FIG. 1.

Please refer to FIG. 4B and FIG. 5A to see the state that engagement protrusions 3341 of the elastic arm parts 334 are engaged with the ring-shaped groove 3221 of the assembly cylinder 322 (i.e., when the angle adjustment knob 330 is located closer to the second angle-adjustment-mechanism connecting part 320). In this moment, the second teeth 33321 on the cylindrical part 333 can be engaged with the first teeth 323 around the assembly cylinder 322 of the second angle-adjustment-mechanism connecting part 320, the angle adjustment knob 330 is in one of the angle adjustment positions and is not able to be rotated relatively to the second angle-adjustment-mechanism connecting part 320, but the first angle-adjustment-mechanism connecting part 310 is still pivotable relatively to the angle adjustment knob 330 and the second angle-adjustment-mechanism connecting part 320. Herein, it can be understood that the angle adjustment knob 330 may have a plurality of angle adjustment positions since the second teeth 33321 can be selectively engaged with different first teeth 323.

Moreover, as the dotted arrows shown in FIG. 4B, the second movement limiting parts 335 of the angle adjustment knob 330 are located between the first movement limiting parts 3121 located at the inner side of the sidewall part 312 of the first angle-adjustment-mechanism connecting part 310, such that the movable range of the first movement limiting parts 3121 is restricted by the second movement limiting parts 335. In detail, the second teeth 33321 of the angle adjustment knob 330 are engaged with the first teeth 323 of the second angle-adjustment-mechanism connecting part 320, and the angle adjustment knob 330 is fixed in one of the angle adjustment positions. Accordingly, the angle adjustment knob 330 is in a non-rotatable state, and the second movement limiting parts 335 are in an immovable state. In this moment, the pivotal movement of the first movement limiting parts 3121 caused by the first angle-adjustment-mechanism connecting part 310 is restricted by the second movement limiting parts 335. As such, the pivotable range of the first angle-adjustment-mechanism connecting part 310 and the second angle-adjustment-mechanism connecting part 320 relative to each other is determined by the relationship among the first movement limiting parts 3121 and the second movement limiting parts 335.

Then, how to use the angle adjustment knob 330 to change the pivotable range of the first angle-adjustment-mechanism connecting part 310 and the second angle-adjustment-mechanism connecting part 320 relative to each other will be described below. Please refer to FIG. 5B, as an external force (such as the pulling force by finger) is applied to pull the angle adjustment knob 330 away from the second angle-adjustment-mechanism connecting part 320, the engagement protrusions 3341 of the elastic arm parts 334 will be engaged with the engagement recesses 3222 of the assembly cylinder 322. By doing so, the second teeth 33321 on the angle adjustment knob 330 will be separated from the first teeth 323 on the second angle-adjustment-mechanism connecting part 320 and thus permitting the angle adjustment knob 330 to be a rotatable state. Then, the angle adjustment knob 330 can be rotated relatively to the second angle-adjustment-mechanism connecting part 320 according to the scale thereon. During the rotation of the angle adjustment knob 330, the engagement protrusions 3341 of the elastic arm parts 334 will sequentially slide over the engagement recesses 3222 of the assembly cylinder 322 and hit the inner wall of the assembly cylinder 322 to make sound feedback due to the elastic property of the elastic arm parts 334. When the angle adjustment knob 330 is rotated to a desired position, the angle adjustment knob 330 can be pushed back and fixed at another angle adjustment position (i.e., the angle adjustment knob 330 is moved back to the non-rotatable state). As a result, the second movement limiting parts 335 of the angle adjustment knob 330 will be changed to different positions compared to that in FIG. 4B, thereby changing the pivotable range of the first movement limiting parts 3121 relative to the second movement limiting parts 355, namely changing the pivotable range of the first angle-adjustment-mechanism connecting part 310 and the second angle-adjustment-mechanism connecting part 320 relative to each other.

Figure 5B:
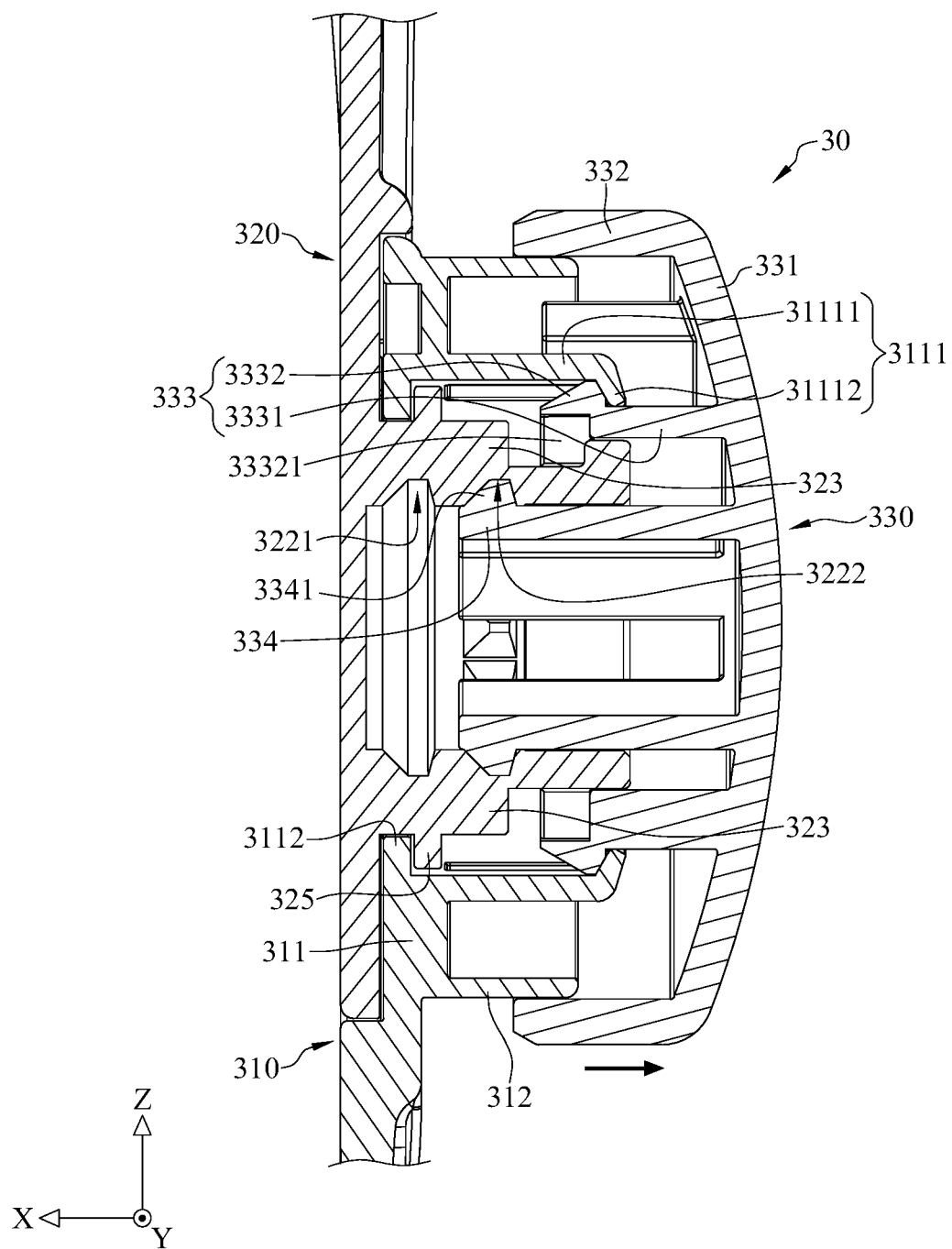
FIG. 5B is a cross-sectional view showing that the angle adjustment knob of the angle adjustment mechanism in FIG. 5A is pulled up.

In short, the wearer can rotate the angle adjustment knob 330 to another position as the angle adjustment knob 330 is in the position shown in FIG. 5B and then push the angle adjustment knob 330 back in place to obtain a different relative position among the first movement limiting parts 3121 and the second movement limiting parts 355 compared to that in FIG. 4B. By doing so, the pivotable range of the first angle-adjustment-mechanism connecting part 310 can be changed so as to restrict the motion of the wearer's limb (e.g., the lower leg).

In addition, as discussed above, the protrusion 3223 of the assembly cylinder 322 is slidably located in the trench 33322 of the cylindrical part 333. As such, the trench 33332 restricts the movable range of the protrusion 3223 and thus restricting the pivotable range of the angle adjustment knob 330 relative to the second angle-adjustment-mechanism connecting part 320 so as to prevent the angle adjustment knob 330 from rotating without limit.

It is understood that the angle adjustment mechanism 30 can be easily disassembled by reversing the above steps during the assemble. In detail, first is to pull up the angle adjustment knob 330 to let the engagement protrusions 3341 of the elastic arm parts 334 to engage into the engagement recesses 3222 of the assembly cylinder 322, second is to rotate the angle adjustment knob 330 until the protrusion 3223 of the assembly cylinder 322 is aligned with one of the openings of the trench 33322 of cylindrical part 333, and then the angle adjustment knob 330 will be able to be detached form the first angle-adjustment-mechanism connecting part 310 and second angle-adjustment-mechanism connecting part 320 along the pivot axis C, and the last is to pivot the first angle-adjustment-mechanism connecting part 310 or the second angle-adjustment-mechanism connecting part 320 to move the engagement parts 325 of the second angle-adjustment-mechanism connecting part 320 to the notches 311b of the first angle-adjustment-mechanism connecting part 310 (i.e., the first angle-adjustment-mechanism connecting part 310 and the second angle-adjustment-mechanism connecting part 320 are returned to the state as shown in FIG. 4A), and then the first angle-adjustment-mechanism connecting part 310 and the second angle-adjustment-mechanism connecting part 320 will be allowed to be detach from each other. As such, it is understood that the assemble and disassemble of the angle adjustment mechanism 30 is not involved with means such as adhering or screwing, that is, the angle adjustment mechanism 30 can be assembled and disassembled in a tool-free manner.

Figure 6A:
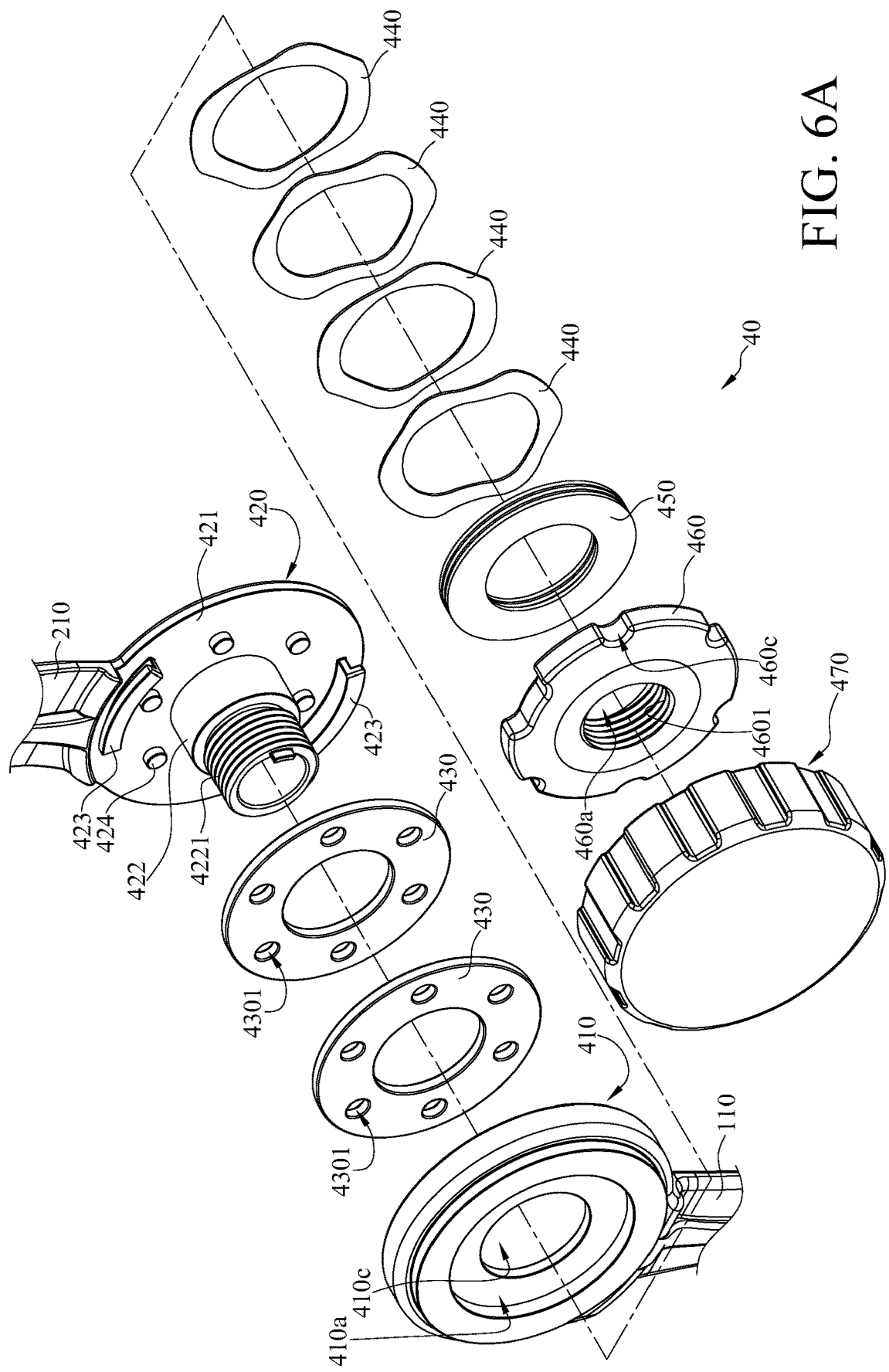
FIG. 6A to 6B are exploded views of a resistance mechanism in FIG. 1 taken at different perspectives.
Figure 6B:
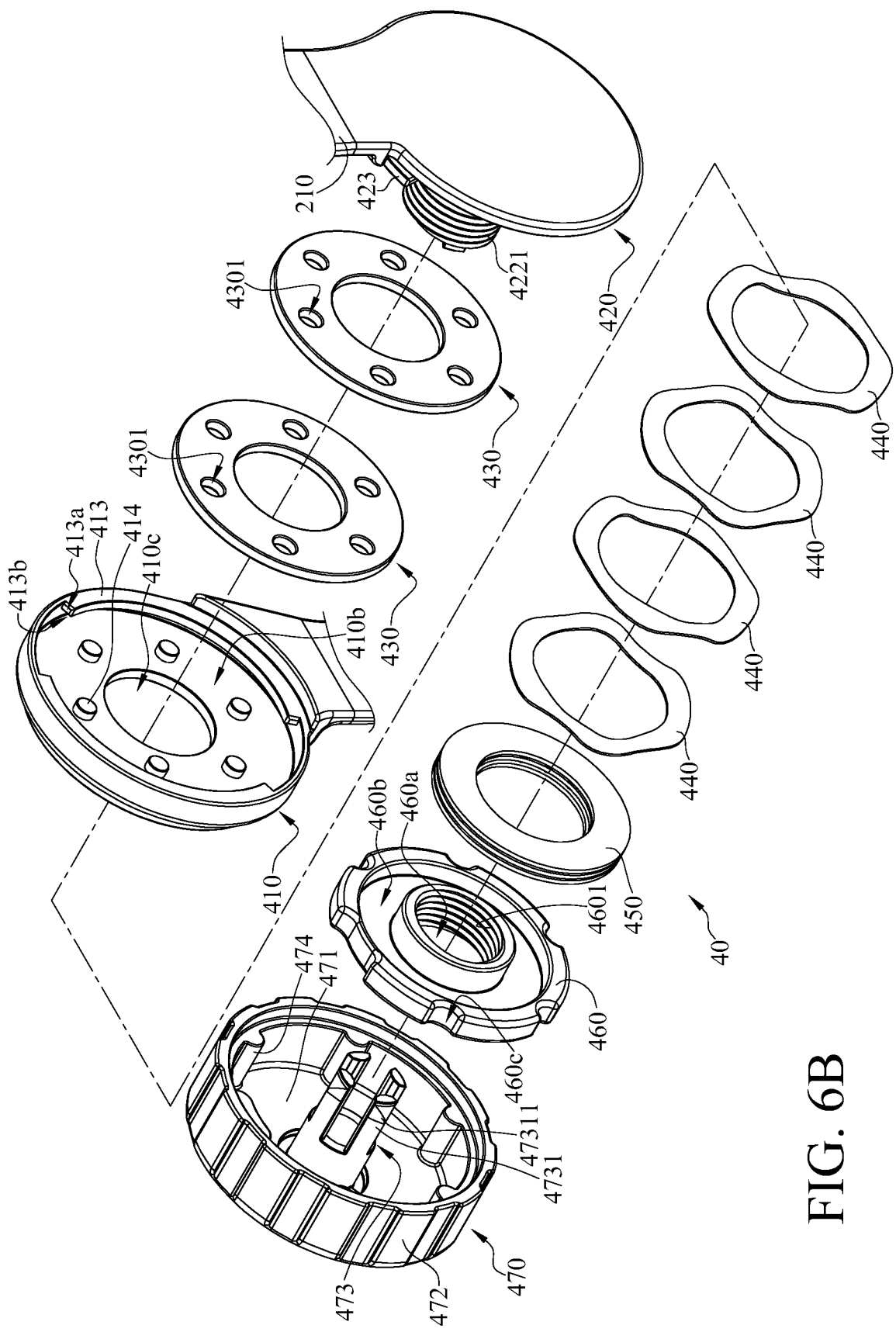
Figure 7:
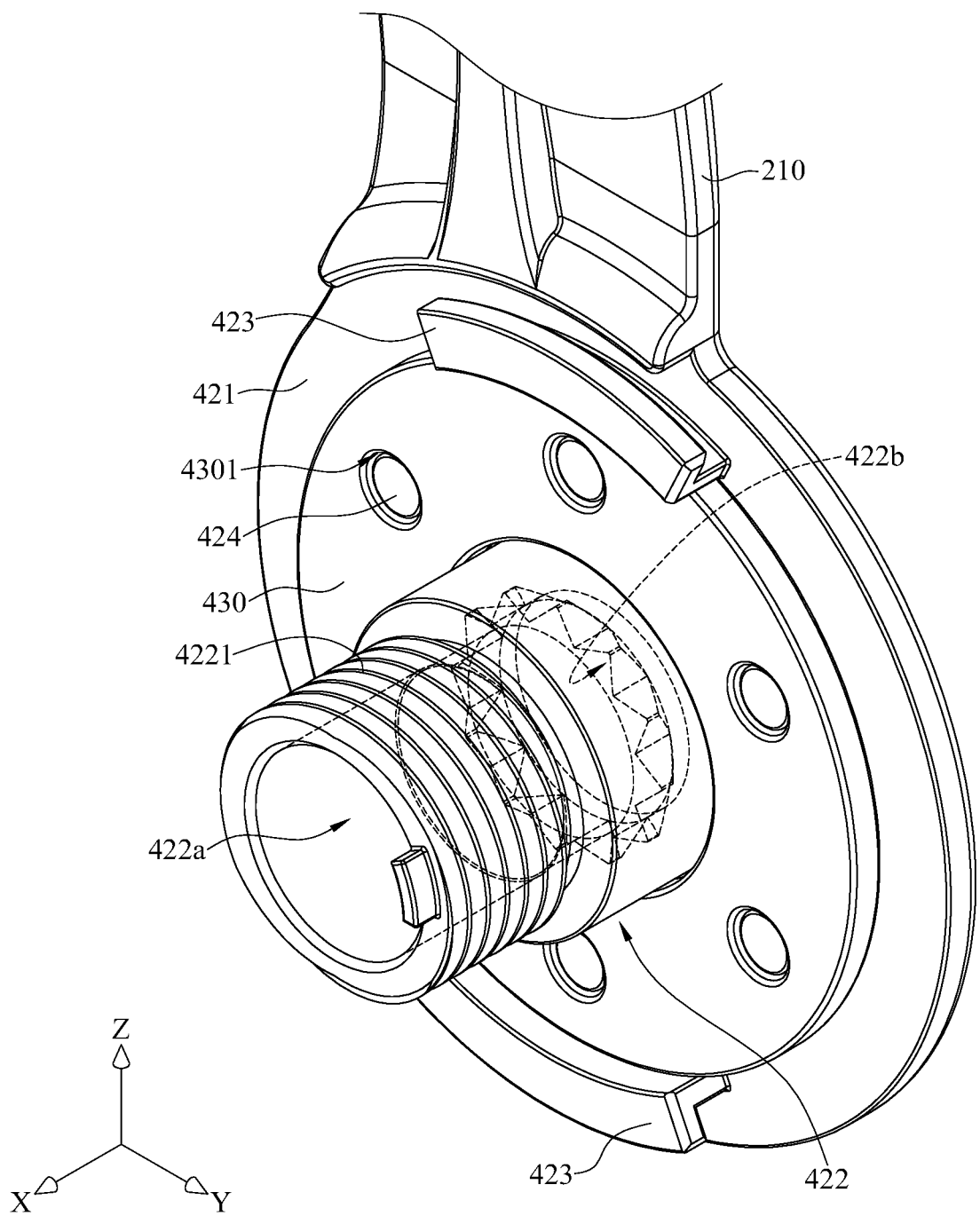
FIG. 7 is a partial enlarged view of the resistance mechanism in FIG. 6A.

Then, the resistance mechanism 40 will be described in more detail below. Please refer to FIG. 6A to 6B and FIG. 7, FIG. 6A to 6B are exploded views of the resistance mechanism 40 taken at different perspectives, and FIG. 7 is a partial enlarged view of the resistance mechanism 40 in FIG. 6A. Meanwhile, please also refer to FIG. 8 to 9A in order to comprehend the relative position of the internal components of the resistance mechanism 40.

In this embodiment, the resistance mechanism 40 includes the aforementioned first resistance-mechanism connecting part 410, the aforementioned second resistance-mechanism connecting part 420, a plurality of friction plates 430, a plurality of elastic components 440, at least one bearing 450, a pressure component 460 and the aforementioned resistance adjustment knob 470.

The first resistance-mechanism connecting part 410 is a ring-shaped plate and has a first installation recess 410a, a second installation recess 410b, a through hole 410c, a plurality of engagement parts 413 and a plurality of positioning protrusions 414. The first installation recess 410a is located at a side of the first resistance-mechanism connecting part 410 facing away from the second resistance-mechanism connecting part 420, and the second installation recess 410b is located at a side of the first resistance-mechanism connecting part 410 facing the second resistance-mechanism connecting part 420. That is, the first installation recess 410a and the second installation recess 410b are respectively located at two opposite sides of the first resistance-mechanism connecting part 410. The through hole 410c is connected to the first installation recess 410a and the second installation recess 410b, and the through hole 410c is located at the center of the first resistance-mechanism connecting part 410.

The engagement parts 413 are located at a side of the first resistance-mechanism connecting part 410 facing the second resistance-mechanism connecting part 420. Further, the engagement parts 413 are located at two opposite sides of the first resistance-mechanism connecting part 410 and are spaced apart from each other, such that notches 413a connected to the second installation recess 410b are formed between the engagement parts 413. In this embodiment, the quantity of the engagement parts 413 is two, and the quantity of notches 413a is also two, but the present disclosure is not limited thereto. Furthermore, the engagement parts 413 are spaced apart from the bottom surface (not numbered) of the second installation recess 410b, such that a groove 413b connected to the notches 413a and the second installation recess 410b is formed between the engagement parts 413 and the bottom surface of the second installation recess 410b.

The positioning protrusions 414 are spaced apart from each other, protrude from the bottom of the second installation recess 410b, and surround the through hole 410c, but the present disclosure is not limited to the shape, quantity, or arrangement thereof.

One of the friction plates 430 may be disposed in the second installation recess 410b of the first resistance-mechanism connecting part 410. In this embodiment, the friction plates 430 are substantially similar in structure and may be made of any material that has a relatively high coefficient of friction, but the present disclosure is not limited thereto. Further, the friction plates 430 each have a plurality of positioning holes 4301. The positioning holes 4301 on one of the friction plates 430 may respectively correspond to and for the insertions of the positioning protrusions 414 of the first resistance-mechanism connecting part 410, but the present disclosure is not limited to the shape, quantity, and arrangement thereof. When one of the friction plates 430 is accommodated in the second installation recess 410b, the friction plate 430 can be fixed in place by the positioning protrusions 414 inserted into the positioning holes 4301 and thus preventing from rotating relatively to the first resistance-mechanism connecting part 410.

The second resistance-mechanism connecting part 420 has a base 421, an assembly cylinder 422, a plurality of engagement parts 423 and a plurality of positioning protrusions 424. The base 421 is connected to one of the second side parts 210 of the second wearable part 20. The assembly cylinder 422 is a hollow structure and extends toward the first resistance-mechanism connecting part 410 from the base 421. The outer diameter of the assembly cylinder 422 is substantially slightly smaller than the diameter of the through hole 410c of the first resistance-mechanism connecting part 410. The assembly cylinder 422 has male outer threads 4221. In addition, as shown in FIG. 7, the hollow assembly cylinder 422 has a bore 422a and a plurality of engagement recesses 422b. The bore 422a is located farther away from the base 421 than the engagement recesses 422b. The engagement recesses 422b are a series of geometric recesses, and the inner diameter of the engagement recesses 422b is larger than the inner diameter of the bore 422a.

The engagement parts 423 have a bent shape. The engagement parts 423 are located at a surface of the base 421 facing the first resistance-mechanism connecting part 410 and are respectively located at different sides of the base 421. The positioning protrusions 424 are spaced apart from each other, protrude from the surface of the base 421 facing the first resistance-mechanism connecting part 410, and surround the assembly cylinder 422, but the present disclosure is not limited to the shape, quantity, and arrangement thereof. In this embodiment, the positioning hole 4301 on the other the friction plates 430 may respectively correspond to and for the insertions of the positioning protrusions 424 of the second resistance-mechanism connecting part 420. When the other the friction plate 430 is disposed on the side of the base 421 facing the first resistance-mechanism connecting part 410, the friction plate 430 is located between the engagement parts 423 and can be fixed in place by the positioning protrusions 424 inserting into the positioning holes 4301 in order to prevent the friction plate 430 from rotating relatively to the base 421 of the second resistance-mechanism connecting part 420.

Figure 8:
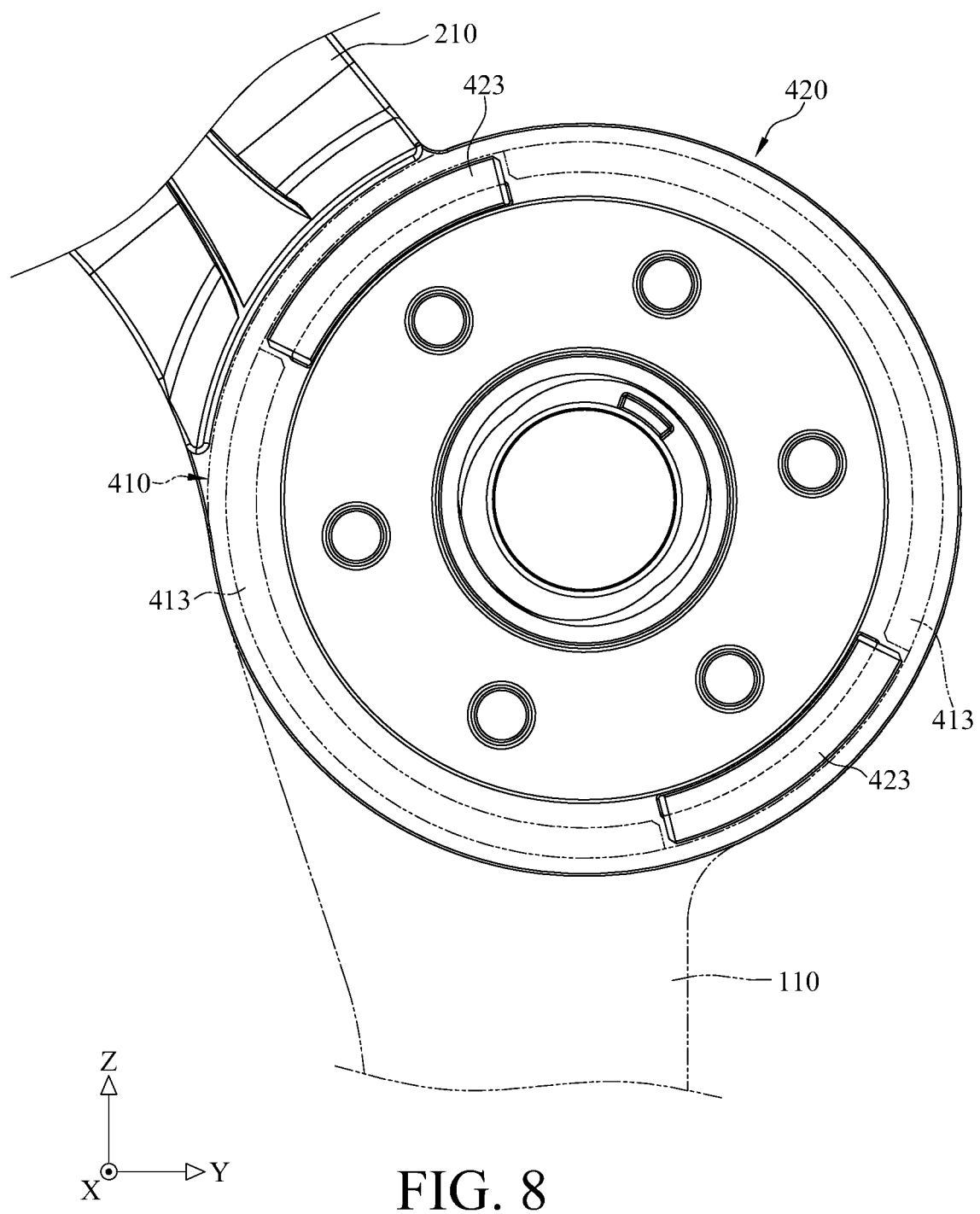
FIG. 8 is a partial side view of the resistance mechanism in FIG. 1 while the resistance mechanism is ready to be detached or assembled.

As the auxiliary lines shown in FIG. 6A to 6B and FIG. 8, the assembly cylinder 422 of the second resistance-mechanism connecting part 420 can be disposed through the through hole 410c of the first resistance-mechanism connecting part 410 so as to assemble the first resistance-mechanism connecting part 410 and the second resistance-mechanism connecting part 420. To do so, the engagement parts 423 of the second resistance-mechanism connecting part 420 should be aligned with the notches 413a of the first resistance-mechanism connecting part 410 so that the engagement parts 423 will be able to be inserted into the groove 413b under the engagement parts 413 of the first resistance-mechanism connecting part 410 via the notches 413a, and then the engagement parts 423 can be engaged with the engagement parts 413. In this moment, the friction plates 430 are in contact with each other in a face-to-face manner. In addition, in one embodiment, the friction plates may be fixed to the first resistance-mechanism connecting part and second resistance-mechanism connecting part by adhering. Alternatively, in some other embodiments, the resistance mechanism may not have the aforementioned friction plates 430; in such a case, the first resistance-mechanism connecting part and second resistance-mechanism connecting part would be made of material with a high coefficient of friction or additionally formed with microstructures to improve the friction between each other.

Then, please refer back to FIG. 6A to 6B, the elastic components 440 are, for example, wave washers which are made of a material that can be repeatedly deformed and has an ability to return from deformation, but the present disclosure is not limited to the material, configuration and type of the elastic component. For example, in some embodiments, the elastic components 440 may be switched with a single object such as a rubber block or a compression spring that has an ability to return from deformation and is compressible. The elastic components 440 can be sleeved on the assembly cylinder 422 that is disposed through the through hole 410c of the first resistance-mechanism connecting part 410, such that the elastic components 440 can be stacked in the first installation recess 410a of the first resistance-mechanism connecting part 410 along the pivot axis C.

The pressure component 460 can be sleeved on the assembly cylinder 422 and stacked on the bearing 450. Specifically, the pressure component 460 has a threaded hole 460a, the inner diameter of the threaded hole 460a is substantially equal to the outer diameter of the assembly cylinder 422, and the pressure component 460 has female inner threads 4601 in the threaded hole 460a. The female inner threads 4601 correspond to the male outer threads 4221 of the assembly cylinder 422. Therefore, the female inner threads 4601 of the pressure component 460 can be engaged with the male outer threads 4221 of the assembly cylinder 422 so that the pressure component 460 can be screwed on the assembly cylinder 422 about the pivot axis C. In addition, the pressure component 460 has an accommodation recess 460b surrounding the threaded hole 460a and located at a side of the pressure component 460 facing the first resistance-mechanism connecting part 410. The bearing 450 is accommodated in the accommodation recess 460b and stacked on the elastic components 440. Further, the pressure component 460 has a plurality of positioning recesses 460c on the edge thereof.

The resistance adjustment knob 470 includes a base 471, a sidewall part 472, an assembly cylinder 473 and a plurality of convex structures 474. The sidewall part 472 extends toward the first resistance-mechanism connecting part 410 (or second resistance-mechanism connecting part 420) from the base 417 and surrounds the base 471. The convex structures 474 are spaced apart from one another and protrude from the inner surface (not numbered) of the sidewall part 472. The pressure component 460 can be accommodated in the space (not numbered) formed between the base 471 of the resistance adjustment knob 470 and the sidewall part 472. It can be considered that the resistance adjustment knob 470 can be sleeved on the pressure component 460 on the assembly cylinder 422. The convex structures 474 on the sidewall part 472 can be respectively engaged into the positioning recesses 460c of the pressure component 460 as the pressure component 460 is accommodated in the resistance adjustment knob 470 (i.e., when the resistance adjustment knob 470 is sleeved on the pressure component 460). As such, the pressure component 460 will be fixed in place and prevented from rotating relatively to the resistance adjustment knob 470. However, the present disclosure is not limited to the manner in which the pressure component 460 is fixed to the resistance adjustment knob 470. For example, in some embodiments, the pressure component may not have the aforementioned positioning recesses and may be fixed to the resistance adjustment knob via adhesive.

Figure 9A:
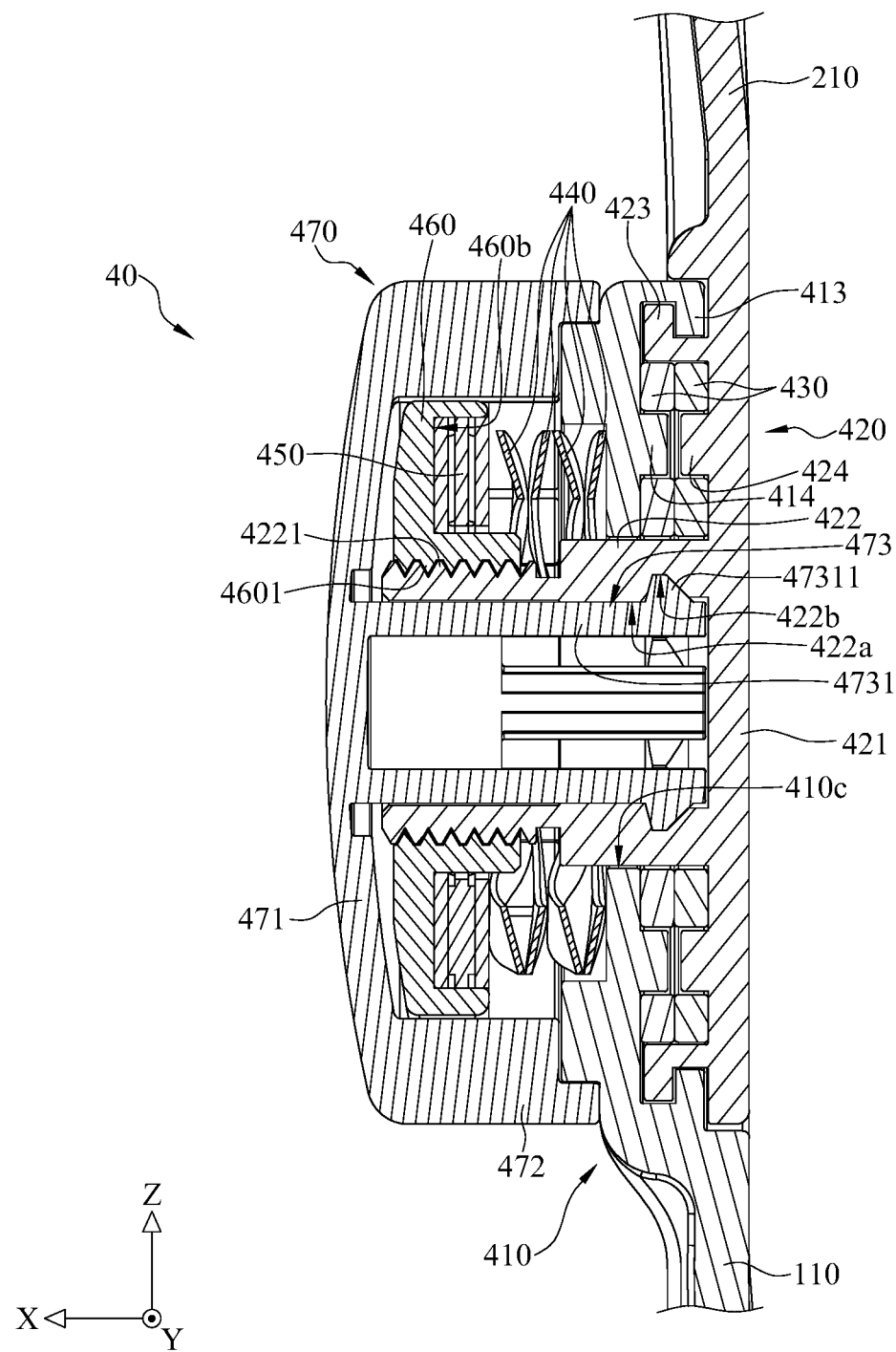
FIG. 9A to 9B are cross-sectional views showing that the resistance mechanism in FIG. 1 in operation.

The assembly cylinder 473 extends toward the first resistance-mechanism connecting part 410 (or second resistance-mechanism connecting part 420) from the base 471. Further, the assembly cylinder 473 includes a plurality of elastic arm parts 4731 that are spaced apart from one another. The elastic arm parts 4731 can be bent or deformed as a certain amount of force is applied thereon. Furthermore, the elastic arm parts 4731 each have an engagement protrusion 47311 protruding from the outer surface of one end facing away from the base 471. The outer diameter of the assembly cylinder 473 where the engagement protrusions 47311 is provided is substantially slightly larger than the inner diameter of the bore 422a of the assembly cylinder 422 but is substantially slightly smaller than or equal to the inner diameter of the engagement recesses 422b of the assembly cylinder 422. Therefore, when the assembly cylinder 473 is disposed into the assembly cylinder 422, the elastic arm parts 4731 are deformed by being forced by the inner wall (not numbered) of the assembly cylinder 422. Until the resistance adjustment knob 470 is kept moving toward the second resistance-mechanism connecting part 420 to let the engagement protrusions 47311 of the elastic arm parts 4731 to be able to engage into the engagement recesses 422b, the elastic arm parts 4731 will be allowed to return from the deformation (as shown in FIG. 9A). In this moment, the resistance adjustment knob 470 is fixed to the assembly cylinder 422 of the second resistance-mechanism connecting part 420 via the assembly cylinder 473. As such, it is understood that the assemble and disassemble of the resistance mechanism 40 is not involved with means such as adhering or screwing, that is, the resistance mechanism 40 can be assembled and disassembled in a tool-free manner.

Accordingly, as shown in FIG. 9A, the elastic components 440 are clamped between the bearing 450 and the bottom surface of the first installation recess 410a of the first resistance-mechanism connecting part 410, such that the elastic components 440 can constantly apply force on the bearing 450 and the first resistance-mechanism connecting part 410 along, for example, the pivot axis C, so as to press the first resistance-mechanism connecting part 410 toward the second resistance-mechanism connecting part 420 to indirectly increase the normal force between the first resistance-mechanism connecting part 410 and the second resistance-mechanism connecting part 420. Therefore, the normal force between the friction plates 430 is increased. As a result, the friction between the friction plates 430 will become a resistance to the motion of the wearer's joint and thus helping to train the muscle around the joint, thereby improving the effect of the rehabilitation.

Figure 9B:
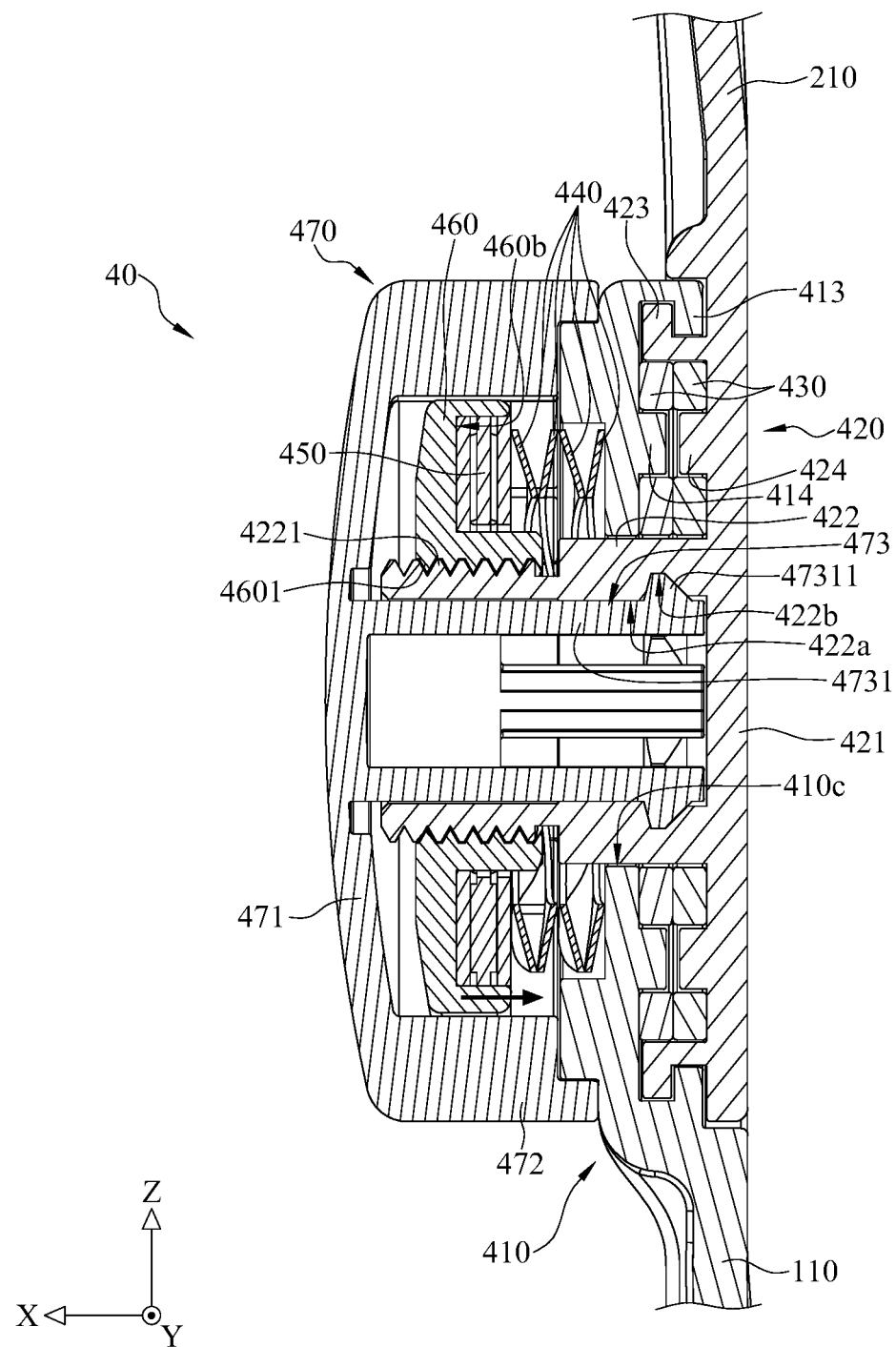

As shown in FIG. 9B, the resistance to the joint can be adjusted by rotating the resistance adjustment knob 470. In detail, when the resistance adjustment knob 470 is rotated in a particular direction according to the designs of the male outer threads 4221 of the assembly cylinder 422 and the female outer threads 4601 of the pressure component 460, the convex structures 474 of the resistance adjustment knob 470 are able to force the pressure component 460 to rotate. During the rotation of the resistance adjustment knob 470, the pressure component 460 can be moved toward the base 421 to further press the elastic components 440 so as to be moved to another pressure applying positions. As shown in FIGS. 9A and 9B, it is understood that the resistance adjustment knob 470 is switchable between at least two pressure applying positions. Consequently, the distance between the pressure component 460 and the first resistance-mechanism connecting part 410 will be changed with the switch of location of the pressure component 460 between different pressure applying positions, such that the elastic components 440 can be pressed harder so as to apply a larger elastic force (i.e., push force) toward the first resistance-mechanism connecting part 410 to further increase the normal force between the first resistance-mechanism connecting part 410 and the second resistance-mechanism connecting part 420 (i.e., to further increase the normal force between the friction plates 430). In such a case, the resistance during the rotation of the first resistance-mechanism connecting part 410 relative to the second resistance-mechanism connecting part 420 can be increased or decreased by rotating the resistance adjustment knob 470, such that the wearer can experience larger or smaller resistance during the motion of the joint. This helps to fit different phases of the rehabilitation. Certainly, the pressure component 460 can further be moved to a pressure applying position that is closer to the first resistance-mechanism connecting part 410 so as to further compress the elastic components 440 to increase the friction between the first resistance-mechanism connecting part 410 and the second resistance-mechanism connecting part 420, but the present disclosure is not limited thereto.

According to the adjustable brace discussed above, the adjustable brace has the angle adjustment mechanism for adjusting the pivotable range of the first wearable part and the second wearable part relative to each other and the resistance mechanism for increasing resistance to the pivotal movement of the first wearable part and the second wearable part. Therefore, the adjustable brace can not only restrict the movable range of the motion of the joint which has been undergone the anterior cruciate ligament reconstruction but also can provide resistance to the motion of the joint to properly train the muscle around the joint, thereby improving the effect of the rehabilitation.

In addition, all of the components of the adjustable brace are detachable, and the assemble and disassemble of the adjustable brace is tool-free, which is convenient for the wearer to assemble, disassemble, detach, clean, or store the adjustable brace.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:
1. An adjustable brace, comprising:
a first wearable part;
a second wearable part;
an angle adjustment mechanism, wherein the angle adjustment mechanism comprises a first angle-adjustment-mechanism connecting part, a second angle-adjustment-mechanism connecting part, and an angle adjustment knob, the first angle-adjustment-mechanism connecting part and the second angle-adjustment-mechanism connecting part are respectively connected to the first wearable part and the second wearable part, the first angle-adjustment-mechanism connecting part has a through hole, the second angle-adjustment-mechanism connecting part has a base and an assembly cylinder, the assembly cylinder protrudes from the base and is disposed in the through hole so that the first angle-adjustment-mechanism connecting part and the second angle-adjustment-mechanism connecting part are pivotably connected to each other, the angle adjustment knob is located at a side of the first angle-adjustment-mechanism connecting part away from the base of the second angle-adjustment-mechanism connecting part and is rotatably fixed to the assembly cylinder of the second angle-adjustment-mechanism connecting part with at least two angle adjustment positions, the first angle-adjustment-mechanism connecting part has at least one first movement limiting part, the angle adjustment knob has at least two second movement limiting parts, and the at least one first movement limiting part is movable between the at least two second movement limiting parts; and
a resistance mechanism,
wherein the first wearable part and the second wearable part are pivotably connected to each other via the angle adjustment mechanism and the resistance mechanism;

wherein the assembly cylinder of the second angle-adjustment-mechanism connecting part has a bore and a plurality of engagement recesses on an inner wall of the assembly cylinder, the angle adjustment knob has at least one elastic arm, the at least one elastic arm of the angle adjustment knob has an engagement protrusion at one end of the at least one elastic arm, the at least one elastic arm of the angle adjustment knob is disposed into the bore of the second angle-adjustment-mechanism connecting part and the engagement protrusion of the angle adjustment knob is located in one of the plurality of engagement recesses of the second angle-adjustment-mechanism connecting part, and the engagement protrusion of the angle adjustment knob is sequentially slid over the plurality of engagement recesses of the second angle-adjustment-mechanism connecting part while the angle adjustment knob is rotated relatively to the second angle-adjustment-mechanism connecting part.

2. The adjustable brace according to claim 1, wherein the resistance mechanism comprises a first resistance-mechanism connecting part, a second resistance-mechanism connecting part, and at least one elastic component, the first resistance-mechanism connecting part and the second resistance-mechanism connecting part are respectively connected to the first wearable part and the second wearable part and are pivotably connected to each other, the at least one elastic component is located at a side of the first resistance-mechanism connecting part not pivotably connected to the second resistance-mechanism connecting part and is configured to provide a normal force between the first resistance-mechanism connecting part and the second resistance-mechanism connecting part along a pivot axis of the first resistance-mechanism connecting part and the second resistance-mechanism connecting part, wherein the resistance mechanism has a coefficient of friction on a place where the first resistance-mechanism connecting part and the second resistance-mechanism connecting part are in contact with each other, and a resistance comes from a frictional force on the resistance mechanism caused by the normal force and the coefficient of friction when the first resistance-mechanism connecting part and the second resistance-mechanism connecting part are pivoted relative to each other.

3. The adjustable brace according to claim 2, wherein the at least one elastic component is a wave washer.

4. The adjustable brace according to claim 2, wherein the quantity of the at least one elastic component is plural, and the elastic components are stacked along the pivot axis of the first resistance-mechanism connecting part and the second resistance-mechanism connecting part.

5. The adjustable brace according to claim 2, wherein the resistance mechanism further comprises a pressure component, the first resistance-mechanism connecting part has a through hole, the second resistance-mechanism connecting part has a base and an assembly cylinder, the assembly cylinder protrudes from the base and is disposed through the through hole so that the first resistance-mechanism connecting part and the second resistance-mechanism connecting part are pivotably connected to each other, the pressure component is located at a side of the first resistance-mechanism connecting part away from the base of the second resistance-mechanism connecting part and is movably fixed to the assembly cylinder of the second resistance-mechanism connecting part with at least two pressure applying positions, the at least one elastic component is clamped between the pressure component and the first resistance-mechanism connecting part, and the pressure component has different distances from the first resistance-mechanism connecting part while being in the at least two pressure applying positions.

6. The adjustable brace according to claim 5, wherein the resistance mechanism further comprises a resistance adjustment knob rotatably assembled to the assembly cylinder of the second resistance-mechanism connecting part, the pressure component is fixed to the resistance adjustment knob, and the resistance adjustment knob is fixed on the assembly cylinder of the second resistance-mechanism connecting part via the pressure component in order to rotate and move the pressure component to the at least two pressure applying positions.

7. The adjustable brace according to claim 6, wherein the assembly cylinder of the second resistance-mechanism connecting part has a bore and a plurality of engagement recesses on an inner wall of the bore, the resistance adjustment knob has at least one elastic arm, the at least one elastic arm of the resistance adjustment knob has an engagement protrusion at one end of the at least one elastic arm, the at least one elastic arm of the resistance adjustment knob is disposed into the bore of the second resistance-mechanism connecting part and the engagement protrusion of the resistance adjustment knob is located in one of the plurality of engagement recesses of the second resistance-mechanism connecting part, and the engagement protrusion of the resistance adjustment knob is sequentially slid over the plurality of engagement recesses of the second resistance-mechanism connecting part while the resistance adjustment knob is rotated relatively to the second resistance-mechanism connecting part.

8. The adjustable brace according to claim 5, wherein the resistance mechanism further comprises a bearing clamped between the at least one elastic component and the pressure component.

9. The adjustable brace according to claim 2, wherein the resistance mechanism further comprises at least one friction plate clamped between the first resistance-mechanism connecting part and the second resistance-mechanism connecting part.

10. The adjustable brace according to claim 9, wherein the at least one friction plate has at least one positioning hole, and the first resistance-mechanism connecting part or the second resistance-mechanism connecting part has at least one positioning protrusion configured to be disposed in the at least one positioning hole.

11. The adjustable brace according to claim 9, wherein the quantity of the at least one friction plate is two, the friction plates are respectively fixed to the first resistance-mechanism connecting part and the second resistance-mechanism connecting part, and the friction plates are in contact with each other in a face-to-face manner.

12. The adjustable brace according to claim 1, wherein the second angle-adjustment-mechanism connecting part further has a plurality of first teeth disposed around an outer surface of the assembly cylinder, the angle adjustment knob further has a plurality of second teeth, and each of the second teeth moves from one of the first teeth to another one of the first teeth while the angle adjustment knob is movable between the at least two angle adjustment positions.

13. The adjustable brace according to claim 12, wherein the first angle-adjustment-mechanism connecting part and the second angle-adjustment-mechanism connecting part have a pivot axis, the angle adjustment knob is movably fixed to the assembly cylinder of the second angle-adjustment-mechanism connecting part along the pivot axis; when the angle adjustment knob is moved close to the base of the second angle-adjustment-mechanism connecting part along the pivot axis, the plurality of second teeth are engaged with the plurality of first teeth so that the angle adjustment knob is in a non-rotatable state; and when the angle adjustment knob is moved away from the base of the second angle-adjustment-mechanism connecting part along the pivot axis, the plurality of second teeth are disengaged from the plurality of first teeth so that the angle adjustment knob is in a rotatable state.

14. The adjustable brace according to claim 1, wherein the first angle-adjustment-mechanism connecting part has a first groove on a side of the first angle-adjustment-mechanism connecting part facing the second angle-adjustment-mechanism connecting part, the second angle-adjustment-mechanism connecting part has an assembly block on a side of the second angle-adjustment-mechanism connecting part facing the first angle-adjustment-mechanism connecting part, and the assembly block is slidably located in the first groove.

* * * * *